(12) United States Patent
Wohlschlager et al.

(10) Patent No.: US 11,382,598 B2
(45) Date of Patent: Jul. 12, 2022

(54) DEVICE AND METHOD FOR DETERMINING FETAL HEART RATE

(71) Applicant: KONINKLIJKE PHILIPS N.V., Eindhoven (NL)

(72) Inventors: Markus Wohlschlager, Sindelfingen (DE); Hansjoerg Geywitz, Kusterdingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 450 days.

(21) Appl. No.: 15/756,999

(22) PCT Filed: Sep. 13, 2016

(86) PCT No.: PCT/EP2016/071530
§ 371 (c)(1),
(2) Date: Mar. 2, 2018

(87) PCT Pub. No.: WO2017/046070
PCT Pub. Date: Mar. 23, 2017

(65) Prior Publication Data
US 2018/0317878 A1    Nov. 8, 2018

(30) Foreign Application Priority Data

Sep. 15, 2015  (EP) .................................. 15185290
Aug. 24, 2016  (EP) .................................. 16185458

(51) Int. Cl.
*A61B 8/08* (2006.01)
*A61B 8/02* (2006.01)
(Continued)

(52) U.S. Cl.
CPC ........ *A61B 8/0866* (2013.01); *A61B 5/02411* (2013.01); *A61B 8/02* (2013.01);
(Continued)

(58) Field of Classification Search
CPC . A61B 8/0866; A61B 5/02411; A61B 8/5269; A61B 8/488; A61B 8/467;
(Continued)

(56) References Cited

U.S. PATENT DOCUMENTS 4,984,576 A    1/1991   Schulenberg et al.
5,123,420 A    6/1992   Paret
(Continued)

FOREIGN PATENT DOCUMENTS

WO    89/09027    10/1989
WO    90/00368    1/1990
(Continued)

OTHER PUBLICATIONS

Mansor, et al., "Simulation of the Generation and Processing of Doppler Ultrasound Fetal Heart Signals to obtain Directional Motion Informatino"; Proceedings of the 28th IEEE EMBS Annual International Conference; 2006-08-30.
(Continued)

*Primary Examiner* — Sanjay Cattungal

(57) ABSTRACT

The invention relates to determining a fetal heart rate from an ultrasonic Doppler echo signal, which comprises at least two channels, including a first channel obtained for a first depth range and a second channel obtained for a second depth range. A first heart rate is determined from the first channel (51, 53, 55) and a second heart rate is determined from the second channel (52, 54, 56). External information on the fetal heart rate and/or the maternal heart rate, extracted from an independent source (60, 61, 62) such as an ECG, is used to select one of the first heart rate and the second heart rate as the fetal heart rate to be determined. A preferred embodiment provides for elimination of double counting heart rates by cutting out unwanted signal contributions. The disclosure further provides for an adaptive
(Continued)

signal processing and data acquisition controlled by patient related data.

6 Claims, 14 Drawing Sheets

(51) Int. Cl.
    *A61B 8/00*            (2006.01)
    *A61B 5/024*          (2006.01)
    *A61B 5/11*            (2006.01)
    *A61B 5/0245*         (2006.01)
    *A61B 5/022*          (2006.01)

(52) U.S. Cl.
    CPC .............. *A61B 8/467* (2013.01); *A61B 8/488* (2013.01); *A61B 8/5269* (2013.01); *A61B 5/022* (2013.01); *A61B 5/0245* (2013.01); *A61B 5/02416* (2013.01); *A61B 5/1102* (2013.01); *A61B 8/5292* (2013.01)

(58) Field of Classification Search
    CPC ......... A61B 8/02; A61B 5/022; A61B 5/0245; A61B 5/1102; A61B 5/02416; A61B 8/5292
    See application file for complete search history.

(56) References Cited

U.S. PATENT DOCUMENTS

| | | | |
|---|---|---|---|
| 5,170,791 A | 12/1992 | Boos | |
| 8,617,076 B2 | 12/2013 | Kabakov | |
| 8,696,578 B2* | 4/2014 | Kabakov | A61B 8/40 600/453 |
| 8,790,261 B2 | 7/2014 | Venugopalan | |
| 2006/0024142 A1 | 2/2006 | Ducret | |
| 2010/0168596 A1* | 7/2010 | Jaeschke | A61B 8/02 600/511 |
| 2010/0235782 A1 | 9/2010 | Powell | |
| 2010/0274145 A1* | 10/2010 | Tupin, Jr. | A61B 5/7278 600/511 |
| 2011/0160591 A1 | 6/2011 | Smith | |
| 2013/0123637 A1* | 5/2013 | Wohlschlager | G01S 7/526 600/453 |
| 2013/0158397 A1 | 6/2013 | Srinivas | |
| 2013/0158406 A1 | 6/2013 | Kabakov | |
| 2013/0158407 A1* | 6/2013 | Kabakov | A61B 8/0866 600/453 |
| 2013/0245436 A1* | 9/2013 | Tupin, Jr. | G01S 13/88 600/430 |
| 2013/0261464 A1 | 10/2013 | Singh | |
| 2014/0276070 A1* | 9/2014 | Kabakov | A61B 8/543 600/453 |

FOREIGN PATENT DOCUMENTS

| | | |
|---|---|---|
| WO | 2009013701 | 1/2009 |
| WO | 2010/035022 | 4/2010 |
| WO | 2012017364 | 2/2012 |
| WO | 2013130979 | 9/2013 |
| WO | 2014/009854 | 1/2014 |

OTHER PUBLICATIONS

Shakespeare, et al., "The information content of Doppler ultrasound signals from the fetal heart", Medical & Biological Engineering & Computing, Springer, Berlin, DE, vol. 39, No. 6, Nov. 1, 2001.
Neilson, et al., "Signal ambiguity resulting in unexpected outcome with external fetal heart rate monitoring"; American Journal of Obstetrics & Gynecology Jun. 2008.
Ragozzino, et al., "Average Fetal Depth in Utero: Data for Estimation of Fetal Absorbed radiation Dose"; Feb. 1986 Radiology, 158, 513-515. Radiological Society of North America, Abstract.

\* cited by examiner

DEVICE AND METHOD FOR DETERMINING FETAL HEART RATE

CROSS REFERENCE TO RELATED APPLICATIONS

This application is the U.S. National Phase application under 35 U.S.C. § 371 of International Application No. PCT/EP2016/071530, filed Sep. 13, 2016, published as WO 2017/046070 on Mar. 23, 2017, which claims the benefit of European Patent Application Number 15185290.2 filed Sep. 15, 2015 and 16185458.3 filed Aug. 24, 2016. These applications are hereby incorporated by reference herein.

FIELD OF THE INVENTION

The invention relates to a processing device for determining a fetal heart rate from an ultrasonic Doppler echo signal, a system for determining a fetal heart rate, a method for determining a fetal heart rate from an ultrasonic Doppler echo signal and a software product for determining a fetal heart rate from an ultrasonic Doppler echo signal.

BACKGROUND OF THE INVENTION

Electronic fetal monitors or Cardio-Toco-Graphs (CTGs) devices for measurement and visualization of normally more than one physiological parameter of unborn human beings and the pregnant mother. These monitors normally include a base unit consisting of a thermal printer and a display unit, and multiple sensor elements for measuring vital parameters e.g. uterine activity of the mother and the heartbeat of the fetus. Basically two methods are used for electronic fetal heart beat monitoring, including an external or indirect method and an internal or direct method.

The external or indirect method employs the use of external transducers placed on the maternal abdomen. Typically, Ultrasound Doppler (US) transducers are used in this category, where high frequency sound waves reflect mechanical action of the fetal heart.

The internal or direct method uses a spiral electrode to convert fetal electrocardiogram obtained from the presenting part of the unborn. This method can be used only when the presenting part is accessible and identifiable.

Both methods, the external and the internal method, have their specific advantages and disadvantages, whereas the Ultrasound Doppler is the preferred method by far over the world, due to the simplicity and noninvasiveness of its application.

There is an interest in (further) improving the existing approaches in order to allow for a consistent and reliable determination, particularly of the fetal heart rate.

SUMMARY OF THE INVENTION

It is an object of the present invention to provide techniques for consistently and reliably determining fetal heart rates.

In a first aspect of the present invention, a processing device for determining a fetal heart rate is presented, wherein the ultrasonic Doppler echo signal comprises at least two channels, the at least two channels including a first channel obtained for a first depth or depth range and a second channel obtained for a second depth or depth range different from the first depth or depth range, wherein the processing unit includes a first processing section and a second processing section, the first processing section being arranged to determine a first heart rate from the first channel of the echo signal, and the second processing section being arranged to determine a second heart rate from the second channel of the echo signal, wherein the processing unit further includes an input section arranged to receive external information on the fetal heart rate to be determined and/or on a heart rate other than the fetal heart rate to be determined, and a choosing section arranged to select one of the determined first heart rate and the determined second heart rate as the fetal heart rate to be determined based on the external information.

In a second aspect of the present invention, a system for determining a fetal heart rate is presented, comprising, in addition to the processing device according to the first aspect, an ultrasonic Doppler device arranged to transmit an ultrasonic signal and to detect an ultrasonic Doppler echo signal and an additional heart rate determining device arranged to determine an additional heart rate independently from the detected ultrasonic Doppler echo signal, the additional heart rate being the fetal heart rate to be determined and/or on a heart rate other than the fetal heart rate to be determined, wherein input section of the processing device is arranged to receive the external information from the additional heart rate determining device.

In a third aspect of the present invention, a method for determining a fetal heart rate is presented, wherein the ultrasonic Doppler echo signal comprises at least two channels, the at least two channels including a first channel obtained for a first depth or depth range and a second channel obtained for a second depth or depth range different from the first depth or depth range, the method further comprises a channel heart rate determining step of determining a first heart rate from the first channel of the echo signal and of determining a second heart rate from the second channel of the echo signal, an input step of receiving external information on the fetal heart rate to be determined and/or on a heart rate other than the fetal heart rate to be determined, and a choosing step of to choose one of the determined first heart rate and the determined second heart rate as the fetal heart rate to be determined based on the external information.

In order to cover a wide variance of maternal body sizes and fetal presentation a wide depth range of the ultrasound beam is normally preferable. Known ultrasound Doppler (US) transducers of devices for measurement and visualization of fetal heart rates utilize an unfocused, approximately cylindrical ultrasound beam field. The extension of the volume of sensitivity is determined by a characteristic time window (receive window), during which the US transducer is susceptible for receiving the reflected signals. Typically the duration of the receive window is designed to cover a wide depth range of approximately 5 to 23 cm. Measurements have shown, that the fetal heart is in average located in a distance of 6 to 10 cm from the surface of the transducer. In order to cover a wide variety of body sizes a great depth range is desirable. It is to be realized, however, that transducers utilizing the Doppler principle are susceptible to frequency shifts caused by all moving structures inside the volume of sensitivity. The signal containing the information of the fetal heart in many cases represents only a small portion of the entire received signal. Signal contributions from other moving structures, like maternal arteries lying behind the fetal heart are frequently superimposed. The signal strength of the unwanted interference signal is influenced by various factors and changes over time. One major factor for influencing the signal strength ratio between fetal and maternal signal are medications. Some tocolytics, for example, are known to increase the signal strength of the maternal heart beat, often dramatically. For selecting the correct heart rate out of a mixture of different superimposed heart rate values the signal strength and the heart rate value itself plays an important role. Fetal heart rate values are normally expected to be between 120 and 160 bpm, whereas the maternal heart rate under normal conditions is far below 100 bpm. Medication and the stress during birth may force, however, the maternal pulse easily up to 160 bpm. Under these conditions conventional algorithms for selecting the correct fetal heart rate may be misguided to select the maternal heart rate instead of the fetal heart rate. Measuring wrong heart rates especially during the second stage of labor is actually a widespread phenomenon. Heart rate alterations caused by maternal and fetal signal interaction are retrospectively difficult to identify and may at worst lead to a misinterpretation.

The first to third aspects of the present invention are particularly aimed at supporting a decision and selection algorithm, which selects exactly the fetal heart rate out of the plurality of heart rates. This may be done by comparing (all) heart rate values coming from the ultrasound Doppler channel with a heart rate derived from, for example, independent transducers or a built in second independent heart rate detection channels. The independent heart rate measuring channel preferably uses different measuring techniques e.g. light absorption, movement detection with accelerometers or electrical activity (ECG). The second channel for calculating a heart rate should preferably ensure that only a maternal heart rate can be calculated (even though the separate channel or source may also provide the fetal heart rate for comparison). An optical method with infrared absorption for example is a very safe and accurate way for retrieving solely the maternal heart rate. Feeding this heart rate to a decision unit of an ultrasound Doppler signal processing algorithm allows the exclusion of a heart rate which is in the range of the heart rate of the second source. The decision and selection algorithm doing the signal scoring then may discard a heart rate value which has the highest scoring, but is most likely a maternal heart rate. In this case a second heart rate value with lower scoring most likely will be the fetal heart rate. If this heart rate has a sufficient scoring and quality the algorithm may output this.

In a preferred embodiment, the additional heart rate determining device includes one or more of an accelerometer unit arranged to measure maternal heart movements, an electrocardiography unit arranged to measure maternal electrocardiography activity, a light sensor unit arranged to measure light absorption indicative of pulsating maternal oxygen saturation, a blood pressure sensor arranged to measure maternal blood pressure, and an additional ultrasonic Doppler unit arranged to determine a heart rate other than the fetal heart rate to be determined.

For the independent heart rate source (additional heart rate determining device), more than one independent source is thinkable. ECG, movement and infrared sensors are easily capable of being integrated into the ultrasound Doppler sensor unit, thus providing more than one source for a maternal heart rate. In addition, the independent maternal heart rate source needs not necessarily be a physical part of the ultrasound sensor. The maternal heart rate values can also be provided by message transmission to the ultrasound signal processing unit from a completely different device for instance from a blood pressure unit. It is also not necessary to provide the maternal heart rate value continuously or as beat to beat values. Spot check values with a fixed or adjusting repetition period should be completely adequate for this purpose, at least as long the depth distribution of the ultrasound Doppler signal sources is not subject of sudden changes.

It is noted that the more independent sources for the maternal heart rate are available, the more reliable is the decision to exclude unwanted heart rates.

In one embodiment a ultrasound transducer with built in two or more processing channels for depth segmentation of the ultrasound Doppler signal contains one or more channels for detecting the maternal heart rate independently. Possible sources could be for example an accelerometer for measuring the pulsating movements caused by the maternal heart, ECG electrodes on the bottom of the transducer housing, which are in direct contact with the maternal skin for measuring the ECG activity or a light sensor for measuring the light absorption caused by pulsating oxygen saturation.

The heart rate values provided by depth segment signal processing channels are compared against the value provided from the independent channel. When selecting a heart rate channel the selection algorithm can then exclude the depth segment which roughly has a heart rate of the independent channel.

In another embodiment, an ultrasound transducer allows message transfer of heart rate values from an external source. Here, the ultrasound transducer with built in two or more processing channels for depth segmentation of the ultrasound Doppler signal is able to receive messages over wired or wireless communication channels from a second transducer (or other source). The second transducer may contain means for an independent determination of one or more heart rates of a known source. For instance a Toco transducer may include an ECG signal processing path. With maternal ECG electrodes attached, the heart rate of this channel is clearly maternal. If a valid heart rate value is available, a message is sent from this transducer as a broadcast to all connected ultrasound transducers. All ultrasound transducers connected to this system can use this information to exclude the depth segment having roughly the value of the message.

In addition or in alternative to the sources listed already above, as sources for independent heart rate values also a heart rate derived from the noninvasive blood pressure measurement, a pulse rate from a SpO2 sensor are contemplated.

When measuring the heart rates of twins or triplets two or more ultrasound transducers are normally in use. Depending of their placement, each transducer may have one or more valid fetal heart rates in different depth segments. In order to prevent the transducers to select all the same depth segment, each ultrasound transducer may communicate by broadcast messages the heart rate value and/or the depth range/segment to the other transducers. Depending on a defined priority, a transducer with lower priority can exclude a depth segment which is already selected by a transducer with higher priority. In a particular case a second ultrasound transducer placed over the maternal heart may be used to exclude the depth segment containing the maternal heart rate of the first transducer.

Furthermore, as discussed above, multiple ultrasound transducers may receive broadcast messages with heart rate values from known independent sources to exclude heart rate values of the depth segments having roughly the same value.

In a preferred embodiment of the invention, the processing device comprises a first demodulation unit arranged to demodulate the echo signal using first channel selection information and a first input frequency based on the carrier frequency of the ultrasonic signal used for generating the echo signal as the demodulation frequency, thus providing a first demodulated signal, and a second demodulation unit arranged to demodulate the echo signal using second channel selection information and a second input frequency based on the carrier frequency of the ultrasonic signal used for generating the echo signal as the demodulation frequency, thus providing a second demodulated signal, wherein the processing device is arranged to selectively operate in one of a channel mode and a phase shift mode, wherein, in the channel mode, the first channel selection information indicates the first channel, the second channel information indicates the second channel and the first and second input frequency are identical, and wherein, in the phase-shift mode, the first channel selection information and the second channel selection information indicate the same channel, wherein there is a shift of 90 degrees in phase between the first and the second input frequency, and the first demodulation unit and the second demodulation unit function, respectively, as the reference demodulation unit and the phase shift demodulation unit, such that the comparison unit is arranged to compare the first and second demodulated signal so to obtain the information on the time-wise relation, wherein the processing device is arranged to switch from the channel mode to the phase-shift mode in accordance with a selection of the choosing section, such that the channel indicated by the first and second channel information is the channel providing the determined heart rate selected as the fetal heart rate.

In this embodiment, there are provided two distinct modes, one of which is directed to addressing the separate channels, so that, based on external heart rate information, the proper channel for the fetal heart beat can be determined by means of parallel processing chains. Once the channel is determined, i.e. where the other channel (or at least one of the other channels) is found as not providing (the best) information on the fetal heart beat, the processing chain previously used for this "discarded" channel is switched to the phase-shifted processing as discussed below with respect to the fourth to sixth aspect. In other words, here the processing chains are used for different purposes depending on the mode of the processing device in total.

In specific implementations, the embodiment may provide for individually configurable signal processing channels controlled by patient data for patient constitution dependent signal processing control, parallel operation of multiple channels using different configurations for measuring multiple sources with one ultrasound transducer (for example twins+mother) and a switchable demodulation method for doubling free heart rate registration.

Particularly, a multiple use of ultrasound Doppler demodulation channels may provide at least some of the following advantages: allowing for segmentations of the volume of sensitivity to increase signal to noise ratio, avoiding double counting if quadrature demodulation is applied, putting aside channels with different evaluation rule sets allows additional background calculations yielding in higher accuracy, parallel heart rate calculation with different rule sets increases the confidence level for measuring the correct heart rate, allowing of a measuring of multiple sources with one transducer (for example twins+mother).

In a fourth aspect of the present invention, a processing device for determining a fetal heart rate from an ultrasonic Doppler echo signal is presented, comprising a reference demodulation unit arranged to demodulate the echo signal using a carrier frequency of the ultrasonic signal used for generating the echo signal as a demodulation frequency, thus providing a reference demodulated signal, a phase shift demodulation unit arranged to demodulate the echo signal using the demodulation frequency shifted by 90 degrees in comparison to the reference demodulation unit, thus providing a phase shift demodulated signal, a comparison unit arranged to compare the reference demodulated signal and the phase shift demodulated signal so to obtain information on a time-wise relation between corresponding respective signal points of the reference demodulated signal and the phase shift demodulated signal, and a processing unit arranged to process the information on the time-wise relation so to determine timing information indicative of first portions of the echo signal corresponding to a movement in a first direction and of second portions of the echo signal corresponding to a movement in a second direction opposite to the first direction, wherein the processing unit is further arranged to use the timing information in a process of determining the fetal heart rate.

In a fifth aspect of the present invention, a system for determining a fetal heart rate is presented, comprising an ultrasonic Doppler device arranged to transmit an ultrasonic signal and to detect an ultrasonic Doppler echo signal, the processing device according to the fourth aspect coupled to the ultrasonic Doppler device for receiving the detected ultrasonic Doppler echo signal.

In a sixth aspect of the present invention, a method for determining a fetal heart rate from an ultrasonic Doppler echo signal is presented, comprising a reference demodulation step of demodulating the echo signal using a carrier frequency of the ultrasonic signal used for generating the echo signal as a demodulation frequency, thus providing a reference demodulated signal, a phase shift demodulation step of demodulating the echo signal using the demodulation frequency shifted by 90 degrees in comparison to the reference demodulation step, thus providing a phase shift demodulated signal, a comparison step of comparing the reference demodulated signal and the phase shift demodulated signal so to obtain information on a time-wise relation between corresponding respective signal points of the reference demodulated signal and the phase shift demodulated signal, and a processing step of processing the information on the time-wise relation so to determine timing information indicative of first portions of the echo signal corresponding to a movement in a first direction and of second portions of the echo signal corresponding to a movement in a second direction opposite to the first direction, wherein the processing step includes using the timing information in a process of determining the fetal heart rate.

In the context of employing the Doppler effect using ultrasound, an incoming Doppler signal (i.e. the echo) is typically extracted from the carrier by means of a synchronous demodulation. This approach is quite simple and does not require high technical effort.

In the context of these aspects of the present invention, it was realized by the inventors that this method has one important drawback, since demodulation is done with the same frequency as the carrier, the direction information respectively sign of the Doppler shift is lost irreversibly.

If this technique is applied for heart beat detection a differentiation between a systolic heart activity and a diastolic heart activity is no longer possible. Both activities appear as two peaks in the time diagram. Under normal conditions the time t1 between systolic and diastolic heart action is significantly lower than the time t2 between the diastole and the systole of the following heart action (see, for example, FIG. 2). The input signal shows two activity peaks, one representing the heart contraction (systole), and the other representing the heart relaxation (diastole). Given the normal framework, according to the Doppler principle systole causes a negative frequency shift and diastole a positive. Since the sign is lost during demodulation the actually unwanted first or second peak of the heart activity can not be identified or eliminated, thus creating unwanted peaks of the autocorrelation function at a higher frequency.

As it becomes clear from the above as well as from the further discussion provided herein, conventional signal processing for ultrasonic Doppler echoes has difficulties in selecting the correct heart rate when the time ratio between two subsequent heart activities reaches one. A straightforward approach from the general theory of signal processing for eliminating doubling could be to remove the unwanted signal components of the heart activity, either systole or diastole. An example of such simple method would be to put the values of the incoming data stream to zero for a defined time after detection of a heart activity. In practice, however, the recorded echo signals are so weak and hidden in the noise that a peak trigger method as used for example to evaluate an ECG signal is not possible. Motion artifacts caused by mother or child produce strong signal fluctuations which make the use of an autocorrelation mandatory. A further possibility to compensate for the loss of movement direction could be to use a demodulation frequency which is higher than the transmission frequency. Suitable filters could then, for example, remove the unwanted frequency components, for example, during diastole. The inventors realized that a technically less demanding and complex solution may be found by using a method like quadrature demodulation. For such quadrature demodulation, the received signal is demodulated with the original transmission frequency and then in parallel with the 90 degrees phase shifted transmission frequency. Comparing the two signals to each other shows that the phase-shifted signal either leads or lags the reference signal.

Information on such leading or lagging can be used for distinguishing between systolic and diastolic movements, wherein this may be used for determining the fetal heart rate as such or may be used for masking unwanted portions of the ultrasound echo signal used for determination of the fetal heart rate, thereby at least reducing detrimental effects of such portions.

The signal points considered in this context are preferably zero crossings of the signals, even though other points may be considered in the alternative or in addition, e.g. points of maximum positive and/or negative amplitude.

In a preferred embodiment, the processing unit is arranged to selectively cut out portions of a demodulated signal obtained by demodulating the echo signal based on the timing information, so to obtain a cut out demodulated signal, wherein the processing unit is further arranged to determine the fetal heart rate using the cut out demodulated signal by means of autocorrelation.

The timing information, eventually including information about the phase of the heart movement, may be used to remove or disregard portions of the ultrasonic Doppler echo signal, thereby allowing for avoiding undesired artifacts. In particular, by cutting out either the systolic or the diastolic heart activity, a doubling is avoided in the autocorrelation.

In a preferred embodiment, the processing unit is further arranged to determine an uncut heart rate by subjecting the reference demodulated signal to autocorrelation and to determine a cut heart rate by subjecting the cut out demodulated signal to autocorrelation, wherein the processing unit further includes a selection section arranged to determine the fetal heart rate by selecting one of the uncut heart rate and the cut heart rate.

It was further found by the inventors that a loss in beat to beat accuracy which might potentially be caused by removing information by means of the cutting out, a heart rate may be determined in parallel by conventional means (e.g. applying autocorrelation on the un-cut or complete ultrasonic Doppler echo signal), while the a comparison of the heart rate obtained from the cut out demodulated signal with a conventionally obtained heart rate may be used for avoiding incorrectly considering the doubled heart rate.

In a preferred embodiment, the processing unit is arranged to subject the timing information to autocorrelation so to obtain the fetal heart rate.

It is possible to use, for example, a stream of signs forming the timing information, to calculate the heart rate by use of an autocorrelation. Either the positive sign or the negative sign or both might be used for correlation. Also possible is the independent evaluation of positive and negative signs.

In a mix of features of the above embodiments, a phase consideration heart rate may be obtained from the timing information by means of autocorrelation, wherein this phase consideration heart rate is used together with a conventionally obtained heart rate to avoid confusion caused by doubled heart rated.

The fourth to sixth aspect of the present invention as discussed above and as discussed with respect to exemplary embodiments referring to the figures are provided in the context of the first to third aspect of the present invention, respectively.

In a seventh aspect of the present invention, a processing device for determining a fetal heart rate is presented, wherein the processing unit is arranged to receive patient related data, the processing unit is provided with setting data relevant to the processing provided by the processing unit, and the processing unit is arranged to adjust the setting data based on the received patient related data.

In an eighth aspect of the present invention, a system for determining a fetal heart rate is presented, the system comprising an ultrasonic Doppler device arranged to transmit an ultrasonic signal and to detect an ultrasonic Doppler echo signal, and the processing device according to the seventh aspect of the invention coupled to the ultrasonic Doppler device for receiving the detected ultrasonic Doppler echo signal, wherein the ultrasonic Doppler device is arranged to receive patient related data, the ultrasonic Doppler device is provided with setting data relevant to its operation, and the ultrasonic Doppler device is arranged to adjust the setting data based on the received patient related data.

In a ninth aspect of the present invention, a method for determining a fetal heart rate is presented, the method comprising a receiving step of receiving patient related data, and an adjustment step of adjusting the setting data relevant to the operation of the method based on the received patient related data.

Especially when used in hospitals, monitors or device for measurement and visualization of physiological parameters like fetal heart beat are connected to a local network infrastructure which connects the monitor with a frequently centralized visualization and archiving program. This program basically is a data base containing all relevant patient data collected over time. CTG trace recordings taken at different times of the pregnancy, medications, anamnesis, patient data and many other physiological parameters are stored and documented in the electronic health record.

Currently, such connected fetal monitors primarily use the electronic health record data base for archiving and storing the data recorded with the applied sensors. Some of the monitors provide special procedures, where a pregnant woman is admitted respectively discharged to a certain labor and delivery room or monitor. After the admit/discharge procedure, the monitor is connected with the data base containing the personal information of the patient. Conventionally, the fetal monitor mainly uses the data base only for dumping the measurement data. Reading information out of the data base to the monitor is only fragmentarily used.

Monitoring the fetal and maternal physiological parameters require very sensitive sensor elements for picking up weak and noisy signals. The level of sensitivity is normally fixed and defined by the experience of the manufacturer to cover a broad range of body constitutions. With the increasing number of overweighed patients obtaining signals with suitable strength is more and more difficult. Simply raising the level of sensitivity for all is not a good way to cover the upper end of the weight scale, because the likelihood of recording unwanted signals increases also. For sensor systems using ultrasound, electric or magnetic fields raising the field strength is also problematic, since in such case normal weighted or underweighted patients would be exposed to unnecessarily high field strength. Furthermore the operating time of battery operated equipment would be reduced unnecessarily. Fetal monitors already offer some simple possibilities of manual adjustments. For example the sensitivity of a Toco sensor can be reduced by 50% in order to avoid clipping of the recording if the sensor is applied to slim women. Adjustment of sensitivity or field energy requires a manual interaction of an operator. Manual interactions are always time consuming and require deep knowledge about the method of operation. Adding additional possibilities of setting adjustment is, on the one hand desirable, but on the other hand it confuses the operator and increases the time for instrument set-up. Reducing the time for instrument preparation and set-up is not unimportant, because in many countries the hospital personnel is reduced, due to economic pressure. Furthermore, all setting changes have to be stored in a memory for recovery after an unexpected power loss. If the monitor does not provide a mechanism for return to the default setting after a patient change, there is a risk of monitoring a new patient with inappropriate settings.

The inventors realized that especially fat has an extremely negative influence on the measurability of all physiological parameters measured during labor and delivery. For adults, overweight and obesity ranges are determined by using weight and height to calculate a number called the "body mass index" (BMI). BMI is used because, for most people, it correlates with their amount of body fat. Patient weight and height, as well as week of gestation are essential parts of the electronic health record. By combining this information, a classification in, for instance three categories fat, normal and slim is easily possible. With this BMI coupled classification, all sensors or transducers connected to a fetal monitoring system can be forced to the point of their optimum performance. The gist of this approach is automating the setting adjustment for each physiological parameter by use of body classification categories. The classification categories may be obtained by, for example, automatic read of relevant data out of the patient health record at the time of admittance, manual entry at the monitor by touch screen or keyboard at the time of admittance, data entry by reading barcode tags or wireless ID tags at the time of admittance.

Adjusting critical measurement settings of each physiological parameter automatically allows for advantages in that measurement performance may be (even significantly) increased due to optimized signal to noise, monitor set up time is reduced, the point of operation is optimized, as also settings may be changed automatically which are not commonly known by operators, the exposure to energy fields e.g. ultrasound is improved and the operating time of battery powered equipment is improved.

In a preferred embodiment, wherein the processing unit is arranged to be coupled with a data base and to receive the patient related data from the data base, provided with a reading section arranged for reading out a data carrier in which patient related data is stored, and/or provided with an interface section which is arranged to allow for an input of patient related data by a user of the processing device.

The seventh to ninth aspect of the present invention as discussed above and as discussed with respect to exemplary embodiments referring to the figures are preferably provided in the context of the first to third aspect and/or the fourth to sixth aspect of the present invention, respectively. Nevertheless, it is also contemplated to provide the seventh to ninth aspects and their embodiments as discussed herein separately, i.e. independently from the first to third aspect of the present invention, or in combination with just the fourth to sixth aspect.

In a further aspect of the present invention a computer program is presented for determining a fetal heart rate from an ultrasonic Doppler echo signal, the software product comprising program code means for causing a processing device according to first, fourth or seventh aspect to carry out the steps of the method according to the third, sixth or ninth aspect, respectively, when the software product is run on the processing device.

It shall be understood that the processing device of claim 1, the system of claim 3, the method for determining a fetal heart rate of claim 5, and the computer program of claim 6 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

FIG. 1 shows a number of diagrams illustrating the concept of autocorrelation.

Firstly, as a non-limiting introduction to the discussion of the autocorrelation, a discussion of an exemplary realization of a determination of a fetal heart beat is given.

An ultrasound Doppler transducer is placed on the abdomen of the mother and held in place by an elastic belt fitted around the waist. The Doppler Effect is based on the principle that sound waves reflected from a moving target are shifted in frequency depending on the direction and speed of movement. Based on this principle, mechanical contractions of the fetal heart muscle lead to periodic signal patterns in the ultrasound reflection. The periodicity of the patterns is used by fetal monitors to determine the fetus' current heart rate. The majority of fetal heart rate transducers use the pulsed-wave principle. An array of piezo elements is used as an electro mechanical converter. This array operates bi-directional as transmitter and receiver. A sequencer controls the timely switch over between transmit and receive phase. During the transmission phase the piezo array is repetitively excited to generate ultrasonic wave packets which are traveling towards the fetal heart. These traveling wave packets are reflected and frequency shifted due to the Doppler effect on moving layers in the body of the pregnant woman, for example at the fetal heart. The received reflected signal is demodulated by a synchronous demodulator utilizing exactly the same frequency as used for the transmit burst. After demodulation, integration, amplification and band-pass filtering the Doppler frequency is available for signal processing. The received weak Doppler shifted echo signal is embedded in noise and signals from artifacts caused by body or transducer movements.

In order to extract the periodic signal out of the noise the method of autocorrelation is applied. Autocorrelation is a mathematical method for finding repeating patterns, such as the presence of a periodic signal which has been buried under noise. The result of the correlation is a function which allows the exact calculation of heart rate.

FIG. 1 shows a simplified illustration how the output of an autocorrelation is calculated. A signal is multiplied with the time shifted copy of itself point wise. The result of each multiplication is summed up.

In FIG. 1, the hatched rectangles show where the product is not zero and thus contributing to the autocorrelation function.

Figure 1A:
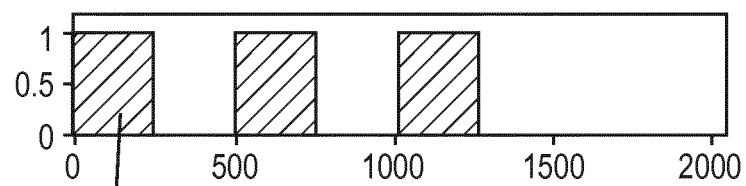
FIG. 1 shows a number of diagrams illustrating the concept of autocorrelation.
Figure 1B:
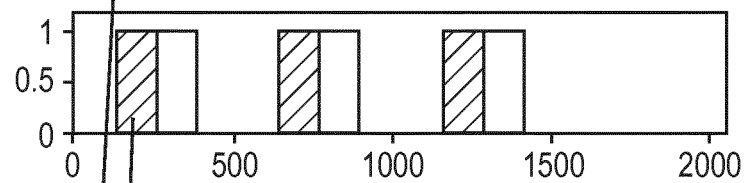
Figure 1C:
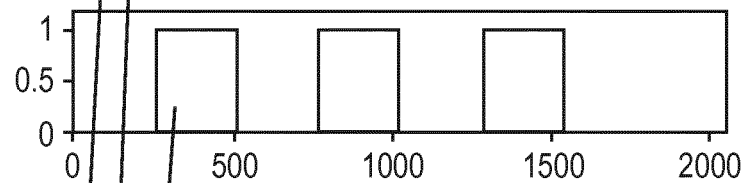
Figure 1D:
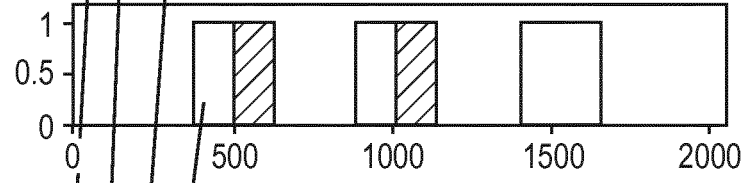
Figure 1E:
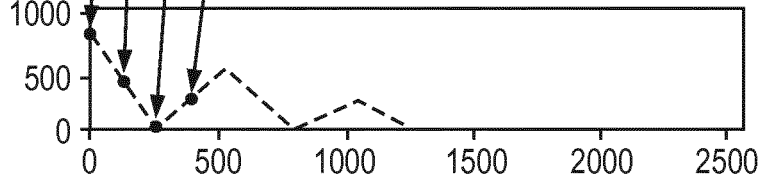

FIG. 1a) shows the case of a time shift 0 ($\tau$=0), where the similarity corresponds to the entire pulse. FIG. 1b) shows the case of a time shift of 128 lags ($\tau$=128), where the similarity corresponds to the half the pulse (3 times over). FIG. 1c) shows the case of a time shift of 256 lags ($\tau$=256), where there is no similarity at all. FIG. 1d) shows the case of a time shift of 384 lags ($\tau$=384), where the similarity corresponds to the half the pulse (2 times over). The result of the autocorrelation is given in FIG. 1e), wherein the arrows point from FIG. 1a) to 1d) to the corresponding portions of the result.

The abscissa of FIG. 1 shows the lapse of time (in lags), while the ordinate is provided with arbitrary units.

At time shift 0 the autocorrelation result (FIG. 1e) has its maximum representing the energy of the signal. At time shift 512 (not shown in FIG. 1a) to d)) the autocorrelation function has a first maximum ($\tau$=512). This peak represents the first repetition of the signals periodicity. In taking the i-value of this peak the signal frequency can be calculated.

Figure 2A:
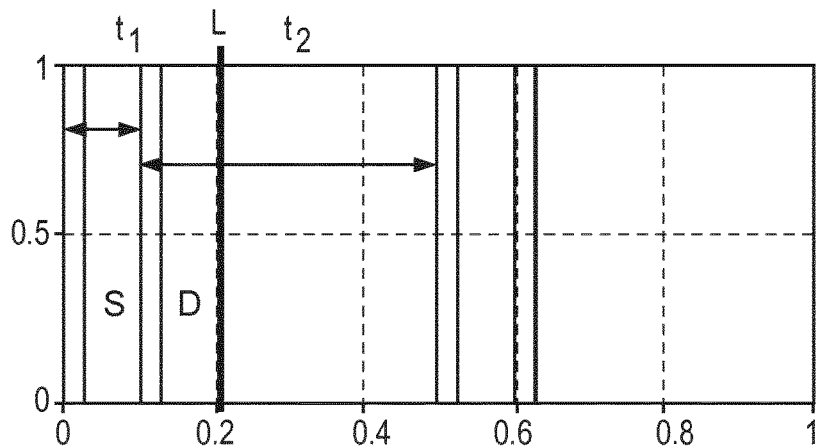
FIG. 2 shows an illustration of for autocorrelation of a non-equidistant simplified heart activity.
Figure 2B:
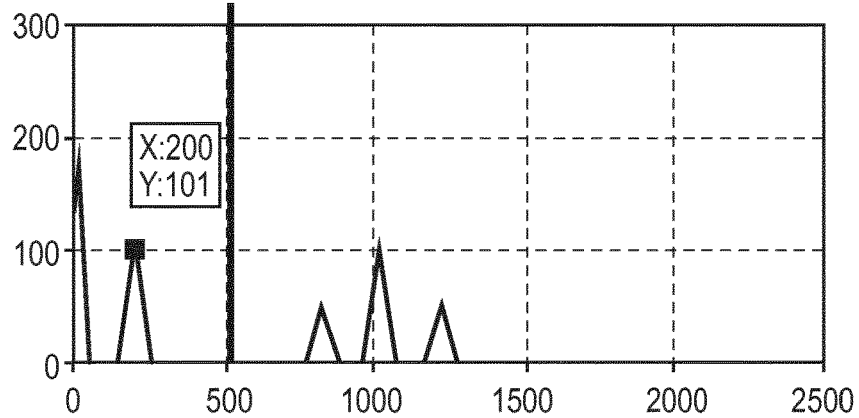

FIG. 2 shows an illustration of for autocorrelation of a non-equidistant simplified heart activity.

Typically, the incoming Doppler echo signal is extracted from the carrier by means of synchronous demodulation, wherein this method is quite simple and does not require high technical effort. The inventors realized that this method has one important drawback in that, since demodulation is done with the same frequency as the carrier, the direction information (respectively sign) of the Doppler shift is lost irreversibly.

If such technique is applied for heart beat detection a differentiation between a systolic heart activity and a diastolic heart activity is no longer possible. Both activities appear as two peaks in the time diagram (see FIG. 2a)). Under normal conditions the time (t1) between systolic and diastolic heart action is significantly lower than the time (t2) between the diastole and the systole of the following heart action.

The input signal shows (FIG. 2a) two activity peaks, one representing the heart contraction (S=systole), and the other representing the heart relaxation (D=diastole). According to the Doppler principle systole causes a negative frequency shift and diastole a positive. Since the sign is lost during demodulation the actually unwanted first or second peak of the heart activity can't be eliminated, thus creating unwanted peaks of the autocorrelation function at a higher frequency.

Given is a periodical heart beat consisting of contraction (S) and relaxation (D) with a frequency of 2 Hz=120 bpm. The time between systole and diastole is 100 ms (the abscissa of FIG. 2a) showing time in units of seconds, the ordinate being normalized). The ACF result (FIG. 2b), with abscissa showing lags and an arbitrarily provided ordinate) shows two peaks with an amplitude of 100, one at τ=200 and the other at τ=1024.

Both peaks have the same amplitude. When calculating the related frequency τ=200 yields in a frequency of 614 bpm, while the second peak at τ=1024 still shows 120 bpm. In order to avoid false HR evaluation the evaluation range of the CTGs using auto correlation is limited to a range of approx. 240 (τ=512) The line L illustrates the peak examination limit.

Peak evaluation and peak selection is done in a second part of the signal processing, the so called post processing. This function normally simply cuts off peaks which have a frequency higher than 240 bpm. The setting of the peak examination limit has an essential effect on the doubling behavior of the monitor. If the setting is at 240 bpm all heart rates above 120 bpm are "doubling save", because if the heart rate is doubled, the result is always outside the evaluation limit. Fetal heart rate traces in the great majority cover the area from 140 bpm to 180 bpm, whereas the maternal heart rate is mostly below 100 bpm.

Besides the evaluation limit setting, probably the most important factor for doubling is the ratio between t1 and t2. If the t1/t2 ratio reaches 1 the heart rate value is doubled with a high likelihood. Unfortunately the ultrasound Doppler sensor is susceptible to all moving structures inside the volume of sensitivity. The signal containing the information of the fetal heart in many cases represents only a small portion of the entire received signal. Signal contributions from other moving structures, like maternal arteries lying behind the fetal heart are frequently superimposed especially if medications increase pulse rate and blood pressure of the mother.

The time ration t1/t2 is important for doubling. Due to the physiology of the human heart, the time ratio t1/t2 is not constant over the heart rate range. It can be said that at heart rates between 80 bpm and 120 bpm the likelihood of reaching a ratio of 1 is high. Doubling a frequency of 80 bpm is then recorded as 160 bmp. This might exactly be the heart rate range expected for a fetus. Cases where the (doubled) heart rate of the mother was recorded over hours due to absence of a fetal heart rate are reported at times.

Figure 3A:
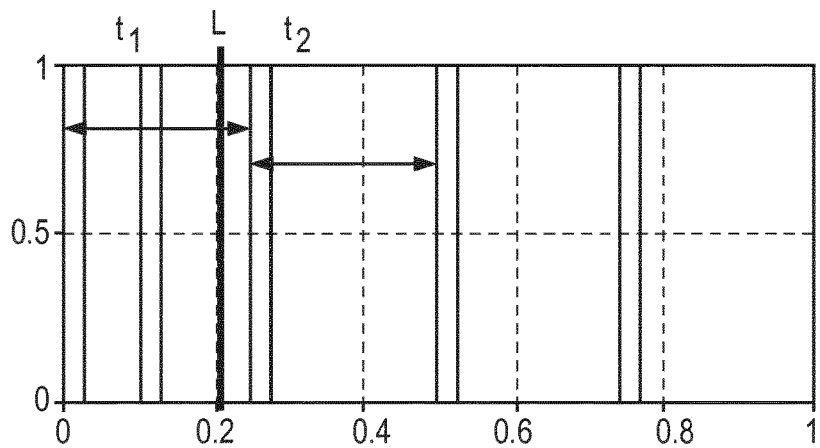
FIG. 3 shows an illustration of for autocorrelation of an equidistant simplified heart activity.
Figure 3B:
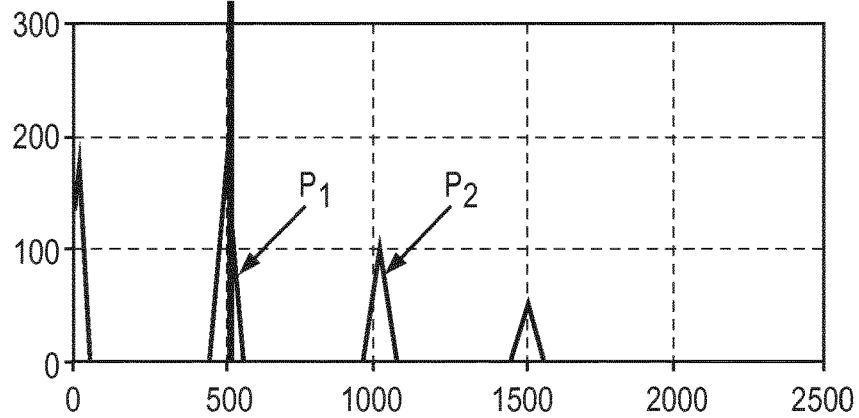

FIG. 3 shows an illustration of for autocorrelation of an equidistant simplified heart activity, in an arrangement similar to that of FIG. 2.

FIG. 3 in particular illustrates the effect of doubling. In the input signal, t1 is prolonged to approximately the same value as t2. As a result the maximum peak (P1), which previously was outside the evaluation limit, is now exactly on the limit line and thus creating a HR value of 4 Hz=240 bpm (τ=512 yields in 4 Hz). The peak evaluation function has to select P1 instead of P2.

Double count is mainly observed in cases of fetal bradycardia, or when the maternal pulse is inadvertently measured. Normally sequences of double count caused by fetal bradycardia can be easily identified and do not pose a risk for wrong trace interpretation, if the maternal heart rate is recorded with an independent heart rate measurement channel (e.g. maternal pulse measured with an infrared sensor). Nevertheless, measuring a doubled maternal heart rate inadvertently is a serious risk, because maternal heart rate patterns can mimic fetal heart rate patterns. The doubling may remain undiscovered for a long time, because the common method of cross channel verification fails in detecting multiples of a heart rate having the identical source.

Figure 4:
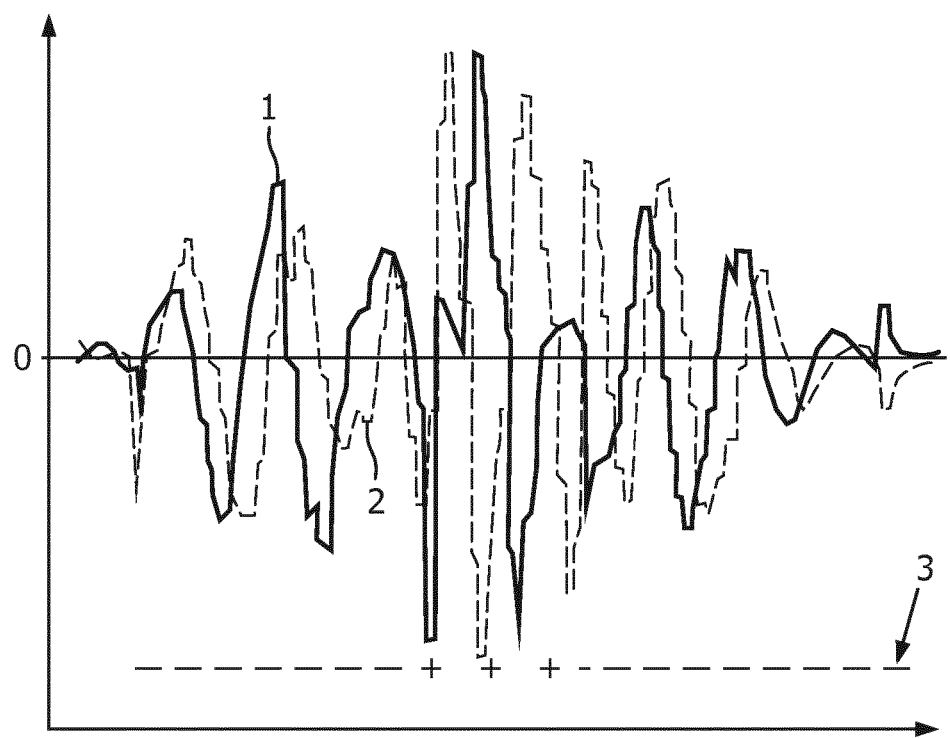
FIG. 4 shows an illustration of phase shifted demodulation of an (artificial) ultrasonic Doppler echo signal.

FIG. 4 shows an illustration of phase shifted demodulation of an (artificial) ultrasonic Doppler echo signal.

In particular, FIG. 4 shows a reference signal (the original artificial Doppler signal) and an artificial Doppler signal demodulated with 90 degrees phase shift. The first signal 1 was demodulated without phase shift, while the second waveform 2 is demodulated with a 90 degree phase shift. In the first half of the wave diagram, the first signal 1 precedes the second signal 2 clearly. At the maximum of the signal amplitude the phasing changes abruptly, from here the second signal 2 precedes the first signal 1 for three oscillations. For the rest of the oscillation the phasing switches back to the initial condition.

Depending on the point of view, the first and the tail part can be seen as a forward movement whereas the central part with the three oscillations could be a backward movement. Measuring a time difference between the zero crossings of the first signal 1 and the zero crossings of the second signal 2, respectively, result in either negative or positive values. For reconstructing the movement direction, basically only the sign without the value is of interest. Evaluating the zero crossings of both signals 1, 2 allows for obtaining a chain of signs 3.

Figure 5:
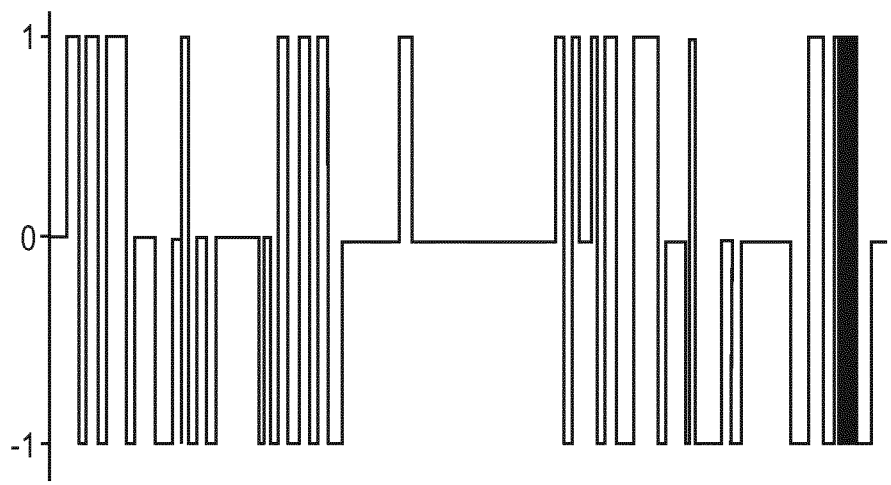
FIG. 5 shows an example of a raw chain of signs corresponding to a phase shifted demodulation as shown in FIG. 4.

FIG. 5 shows an example of a raw chain of signs corresponding to a phase shifted demodulation as shown in FIG. 4.

FIG. 5 shows a typical sequence of signs in a raw form. Noise and overlaid inverse moving parts in the measurement area are reasons for strong sign fluctuations as shown in FIG. 5 (the value 0 indicating that either there was no difference between the zero crossings or the results was indeterminate).

Figure 6:
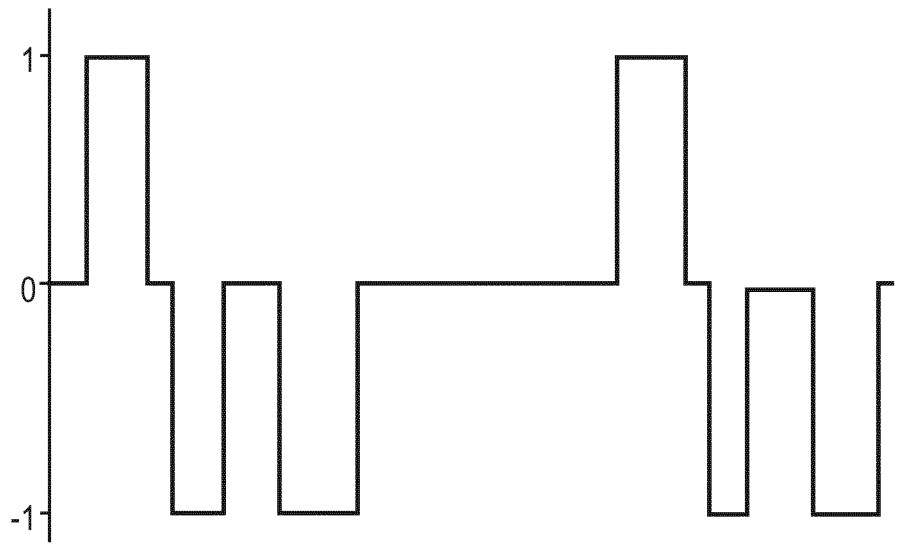
FIG. 6 shows an example of a processed chain of signs derived from the raw chain of signs illustrated in FIG. 5.

FIG. 6 shows an example of a processed chain of signs derived from the raw chain of signs illustrated in FIG. 5.

Applying known and appropriate signal processing methods to the chain of raw signs shown in FIG. 5 yields a smoothened sign signal as shown in FIG. 6, which can be used for further signal processing.

Figure 7:
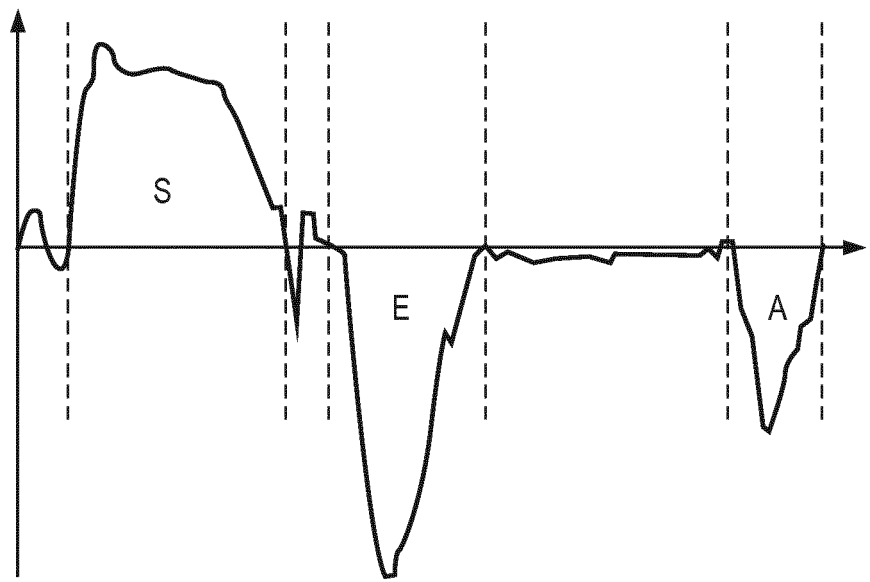
FIG. 7 shows a typical example of an expected velocity profile of a heart activity.

The sign shown in FIG. 6 correlates very well with the expected velocity profile of a heart activity as shown in FIG. 7.

Bearing in mind the different scaling of the abscissa, it can be seen that the smoothened sign signal shown in FIG. 6 represents the velocity direction of a heart activity very well, so it can be used to cut out unwanted parts of the signal. In other words, the inventors realized that the binary sign values may be used to gate the reference signal.

Figure 8:
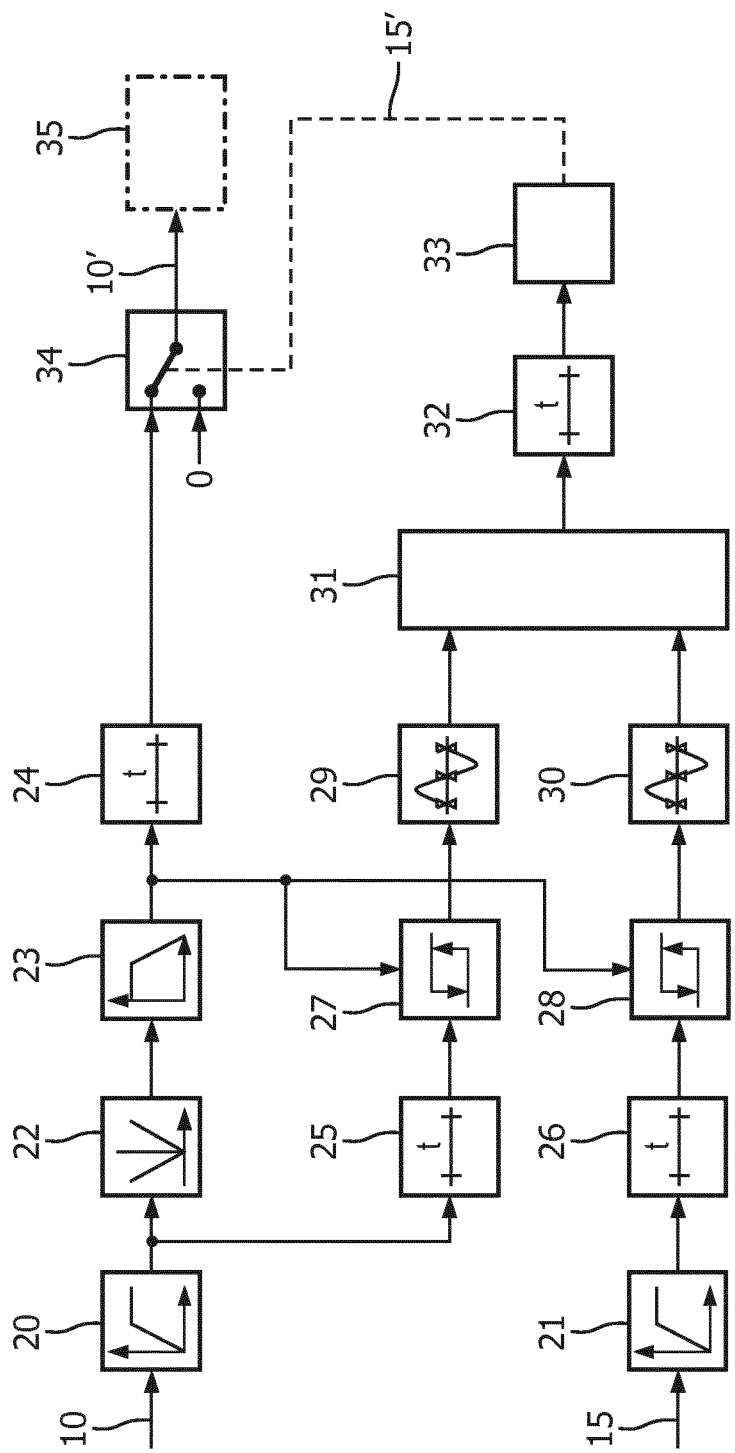
FIG. 8 shows a basic signal processing path for avoiding doubling in accordance with an element of the present disclosure, FIG. 9 allows for a comparison of a conventionally rectified and filtered signal and a gate-controlled signal processed according to an element of the present disclosure.

FIG. 8 shows a basic signal processing path for avoiding doubling in accordance with an element of the present disclosure.

This element provides for by cutting out undesired signal episodes that are identified by their movement direction, respectively sign. A reference signal (reference demodulated signal) 10 demodulated with 0 degree phase shift and a second signal (phase shift demodulated signal) 15 demodulated from the same source with 90 degree phase shift are fed to respective high pass filters 20, 21 to remove DC offset. The reference signal 10 passes the conventional signal processing chain required as preparation for an autocorrelation (i.e. magnitude processing 22, low pass filter 23 and delay 24).

Both signals are tapped after the high pass filters 20, 21. The high passed signals are delayed (blocks 25, 26) to compensate the smoothing filter delay of the approximated envelope. Afterwards these signals are passed through an envelope controlled noise gate 27, 28, respective, to avoid sign detections on plain noise signals e.g. during mechanical pause periods. The next stage for both signals is a respective zero crossing detector 29, 30. By comparing the timely relationship of the two outputs of the zero crossing detectors 29, 30, a sign detector 31 decides if the signal has a positive or a negative sign. A stream of positive, negative or uncertain polarity (no zero crossing or noise) signs is filtered, delayed and smoothened (blocks 32, 33) to obtain a signal as shown in FIG. 6. The resulting binary sign signal 15' (see FIG. 6) is used to cut out unwanted signal episodes with the use of a switch 34. After the switch 34 the processed reference signal 10' has only the signal parts of one heart activity. By cutting out the systolic or diastolic heart activity the following autocorrelation 35 has no longer the chance for doubling.

Figures 9A, 9B:
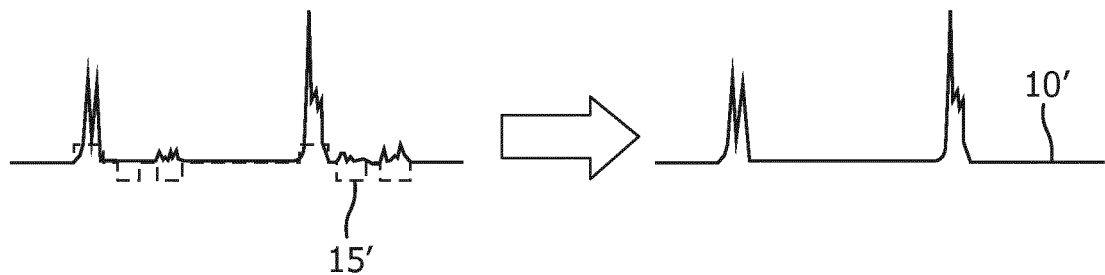

FIG. 9 allows for a comparison of a conventionally rectified and filtered signal and a gate-controlled signal processed according to an element of the present disclosure.

The effect of cutting out episodes of the heart activity as discussed above is shown in FIG. 9. A rectified and filtered signal (FIG. 9a) which is normally used for correlation has to pass a gate controlled by the sign signal 15'. In this example signal activities having a negative sign are blocked. The result is the adjusted signal 10' which is "doubling free".

Here, a signal processing sequence as shown in FIG. 8 is used to avoid double counting. This implementation has the advantage that no additional autocorrelation is necessary. The provided enhancements compared with a traditional implementation include that a second hardware channel for quadrature demodulation and zero crossing detection and sign evaluation including filtering.

However, as the signal loses information, even though the result of the autocorrelation actually is doubling free, it might suffer loss of beat to beat accuracy.

Figure 10:
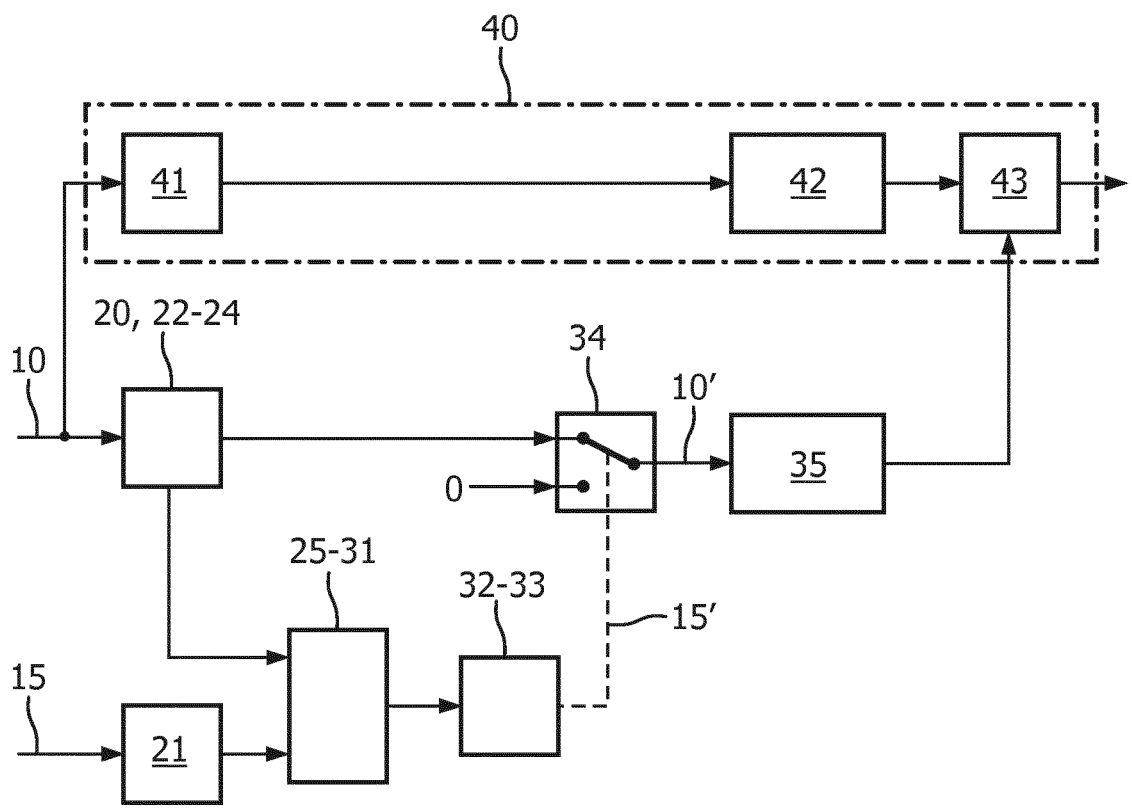
FIG. 10 shows a signal processing according to a second element of the present disclosure.

FIG. 10 shows a signal processing according to a second element of the present disclosure.

In order to avoid a loss of beat to beat accuracy a preliminary fetal heart rate (uncut heart rate) is calculated element additionally using a somewhat conventional approach 40, i.e. including reference signal preprocessing 41 followed by autocorrelation 42. In parallel a second heart rate is calculated according the processing scheme of FIG. 8. A second heart rate (cut heart rate) is used to prevent the heart rate selector 43 of the first autocorrelation to wrongly take a doubled heart rate.

Figure 11:
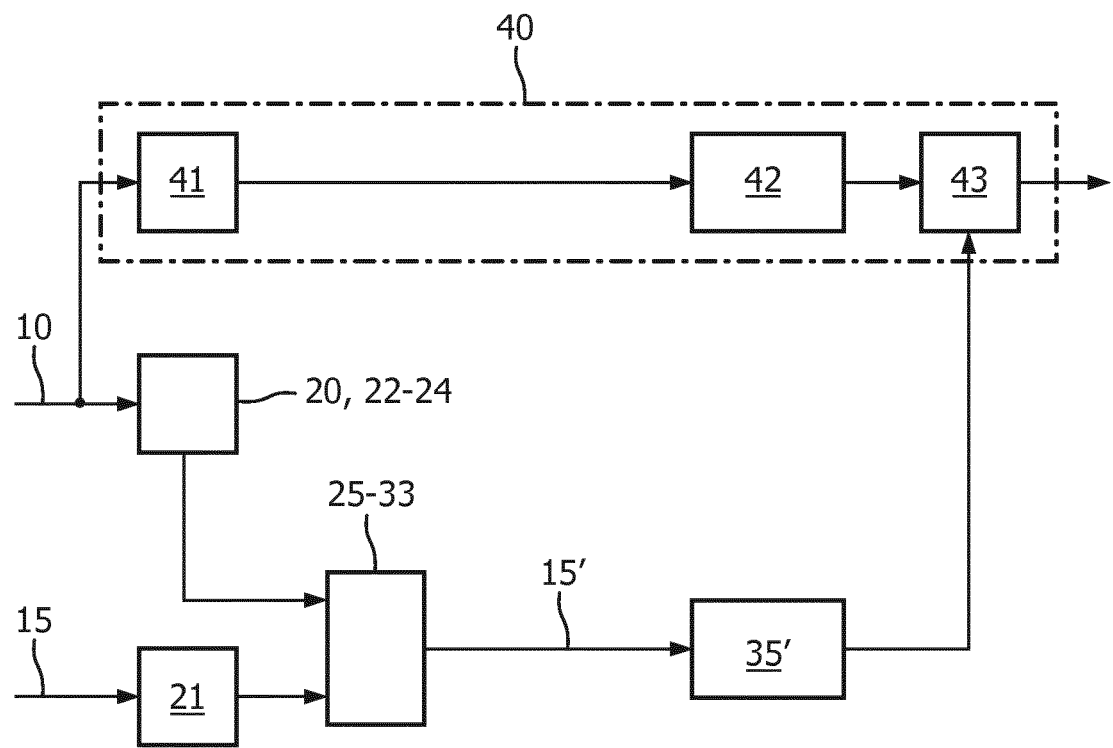
FIG. 11 shows a signal processing according to a third element of the present disclosure.

In a variation of the above, the second heart rate may be directly obtained from the sign stream 15', as it is shown in FIG. 11.

According to the element of the disclosure in FIG. 11, the autocorrelation (and postprocessing) 35' is provided on sign stream or signal 15' (rather than on the cut ultrasonic echo signal 10').

Figure 12:
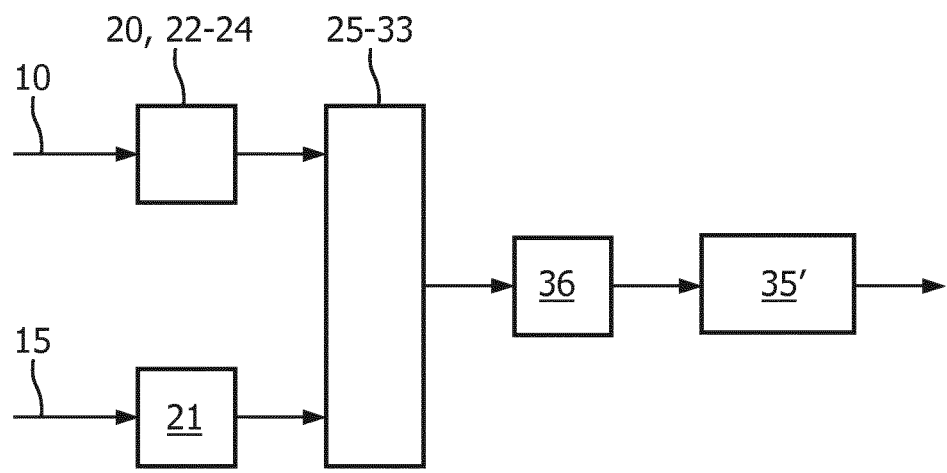
FIG. 12 shows a signal processing according to a forth element of the present disclosure.

FIG. 12 shows a signal processing according to a forth element of the present disclosure, where the heart rate obtained from the sign stream itself is used. Provided is here additionally a sign selection 36 for either the positive sign or the negative sign.

It is to be noted that also both signs might be used for correlation, either in combination or a course of independent evaluation of positive and negative signs.

Corresponding elements in FIGS. 8, 10, 11 and 12 are indicated by corresponding or similar reference signs and additional explanation thereof is therefore omitted.

Figure 13:
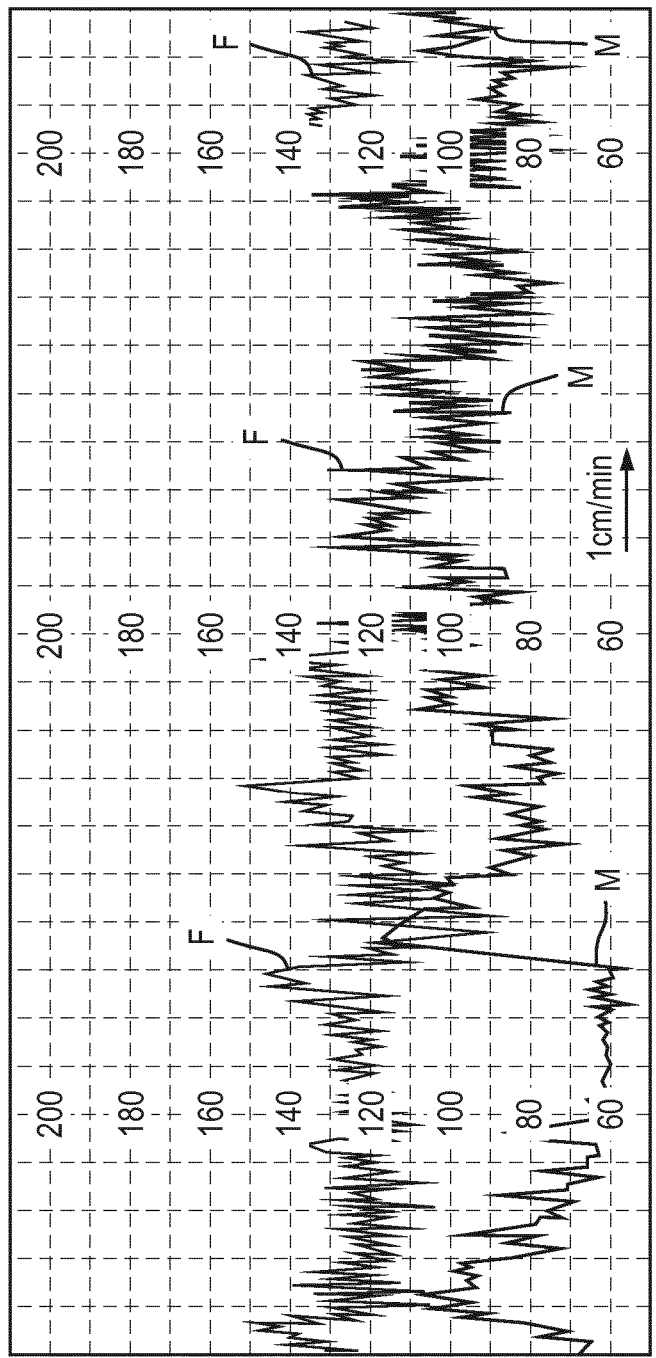
FIG. 13 shows an example of a cardiotocogramm with fetal and maternal heart rate traces.

FIG. 13 shows an example of a cardiotocogramm with fetal and maternal heart rate traces.

The trace snipped of a cardiotocogramm illustrated in FIG. 13 shows two traces F, M. The upper trace F represents a fetal heart rate trace derived from an ultrasound Doppler transducer. The lower trace M shows the maternal heart rate derived with an infrared sensor build into the transducer measuring the uterine activity.

For this example two spatially separated independent heart rate channels are considered. During the first half of FIG. 13, the two traces are clearly separated. There is no doubt about the correctness of the recording of the fetal heart rate. In the second half of the picture the two traces F, M are nearly congruent. Without the information of the maternal trace M, the fetal trace F would be interpreted as a fetal trace, but in this example de facto the ultrasound algorithm unintentionally switched to the maternal heart rate M, which has, due to the scoring and selection algorithm a better score than the lower scored fetal heart rate values. A modified selection algorithm according to the present invention would either select the lower scored fetal heart rate for printing or if no alternative heart rate is available suppress (blank) the printing.

The current status of printing two heart rate values (both in black, because a typically used thermoprinter does not allow color prints) is unsatisfactory, as the user has to decide which of the printed heart rates is a valid fetal heart rate, if the heart rates are nearly congruent the overprinting blurs the fetal heart rate, and a possibly available alternative heart rate is suppressed.

The cross comparison provided by here improves the reliability of a fetal heart rate trace recorded with an ultrasound Doppler transducer. It reduces the likelihood of an unintended switch over to the maternal heart rate. Heart rate alterations caused by the switch over effect may mislead the trace interpretation. Misinterpreting a wrong heart rate trace can cause unnecessary actions, unnecessary surgery, and delayed delivery of a compromised fetus or even fetal death.

Conventional fetal monitors use ultrasound Doppler technology for non-invasive acquisition and recording of the fetal heart rate during gestation and labor. The mechanical contraction of the fetal heart muscle leads to periodic signal patterns in the ultrasound reflection. The period of the patterns is used by fetal monitors to determine the fetus' current heart rate.

A major issue of this technology is its indifference for the physiological signal source which generates the ultrasound reflection. All periodic movements of tissue or blood flow in range of the used ultrasound beam can generate a heart rate pattern. Especially pulsations of the mother's abdominal arteries are a known cause for this problem.

The inventors realized that the different signal sources are spatially separated.

An ultrasonic transducer is placed on the abdomen of a pregnant woman. During the transmission phase the piezo array is repetitively excited in order to generate ultrasonic wave packets which are traveling towards the fetal heart. These traveling wave packets are reflected and frequency shifted due to the Doppler effect on various moving layers in the body of the pregnant women and the child for example from the fetal heart and a maternal artery. Since the fetal heart and the maternal artery are in different distances relative to the surface of the transducer, the wave packets requires different traveling times down to the point of reflection and back to the transducer.

Figure 14:
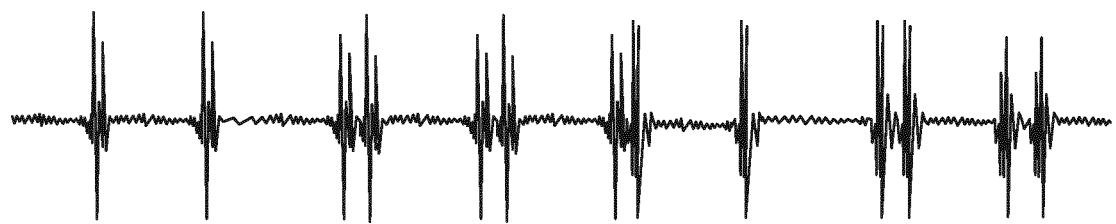
FIG. 14 shows a combined ultrasound Doppler signal resulting from superposition of a fetal heart signal and a maternal heart signal.

The piezo element array is used in both directions. When transmission has finished, the transducer switches from transmit to receive mode. With only one receive window covering the entire measurement depth a signal superpositioning of a signal from a fetal signal source and a maternal source would be the result, as it is illustrated in FIG. 14.

Such a signal makes it difficult for the signal processing unit to extract the correct heart rate.

For this reason multiple receive channels are employed which are active at different times of a measurement cycle.

As already said, the echo signals from different depth require different traveling times until they receive the surface of the transducer. The timely staggered signal acquisition with multiple receive channels allows a proper signal separation.

Figure 15:
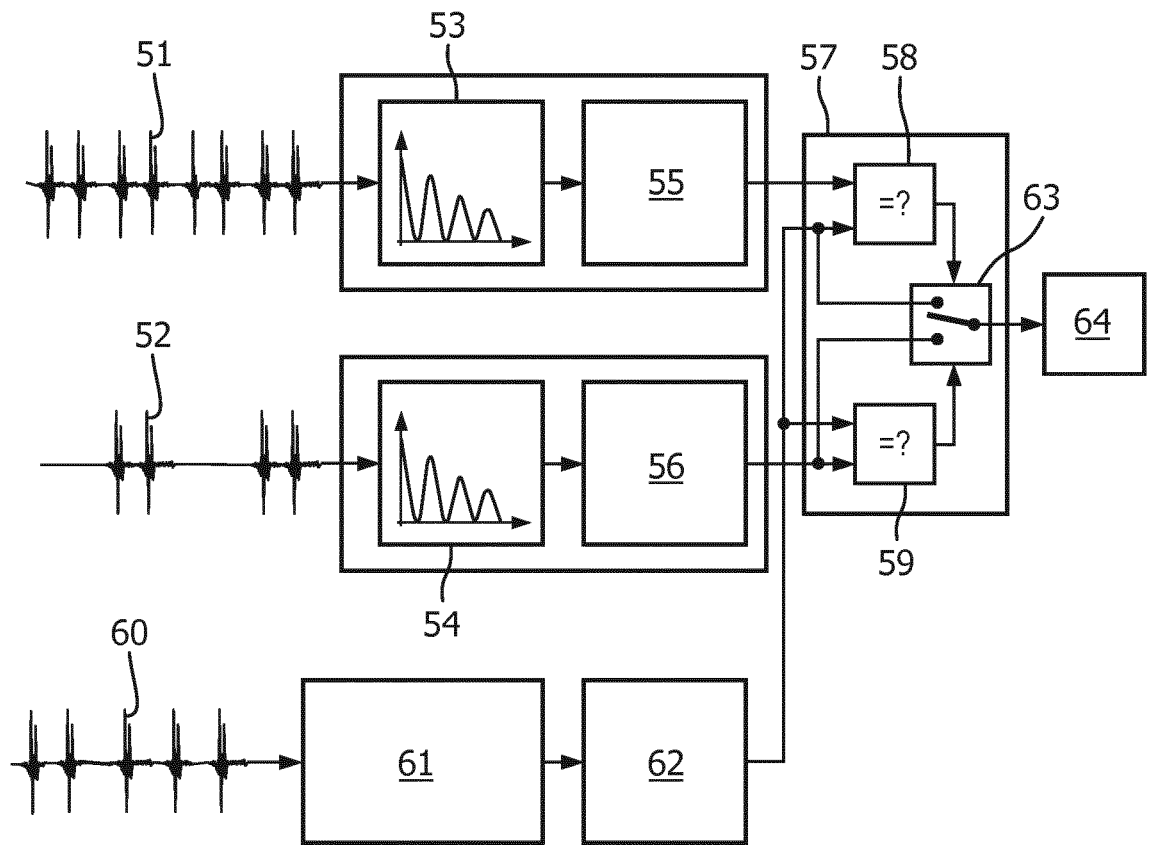
FIG. 15 illustrates a signal processing according to an embodiment of the invention, FIG. 16 schematically shows a further element of the present disclosure, FIG. 17 schematically shows another element of the present disclosure, FIG. 18 schematically shows a yet further element of the present disclosure, FIG. 19 schematically shows a processing device in accordance with another embodiment of the invention.

FIG. 15 illustrates a signal processing according to an embodiment of the invention.

FIG. 15 shows the timely hashed signal of FIG. 14 as input signals 51, 52 for a respective autocorrelation 53, 54. For timely (depth) separation of the superimposed ultrasound Doppler signal discrete demodulation and filtering channels are used, but not shown here, as the skilled person is well familiar with ultrasound signal demodulation and filtering.

The implementation method can vary depending on availability of demodulation and filtering paths provided by the hardware.

At least two (independent) demodulation and signal processing channels are required to implement a basic depth splitting as provided by this embodiment. A good implementation trade-off between signal processing power and hardware complexity is a four channel system.

In order to keep the complexity low the description of the embodiment here uses only two channels.

The digitized ultrasound Doppler signals are then processed in a traditional way by autocorrelation 53, 54 and post processing 55, 56 of the autocorrelation results. The output of each signal processing chain is a heart rate value.

Assume that first depth channel is 145 bpm (upper branch 51, 53, 55). The example further assumes that the depth range of this channel is closer to the surface than the other which yields a heart rate of 68 bpm.

In the simplified setup these two heart rate values will be available for comparison. The values of the ultrasound depth channels are compared 58, 59 in the next step 57 with the value of the independent source 62.

The independent source used, for example, a ECG, which is subjected to processing 61 and determination 62 of a heart rate.

If one of the values is close to the value of the independent source the following algorithm 63 can exclude this value and output 64 the fetal heart rate.

For improving the decision algorithm the depth information of the ultrasound can be used to increase the accuracy for exclusion. For example, if the transducer is positioned traditionally with ultrasound beam directed versus the backbone, the heart rate calculated from the channel with higher traveling time has the signal source farther away from the surface of the transducer. If, in this example the heart rate which matches the value of the independent source and the depth range is behind the layer of the other heart rate, the source of this heart rate is undoubtedly maternal. For the usual transducer positioning this is always true, because the maternal blood vessels are spatially located behind the fetal heart, but if the beam is directed from the back or even laterally, this heuristic approach does not work.

Figure 16:
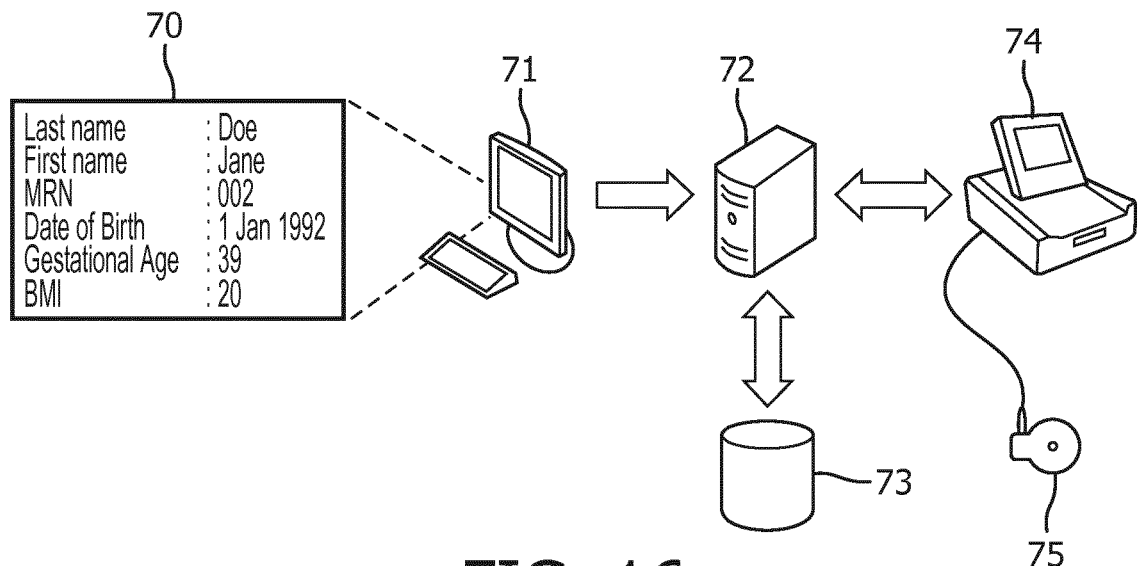

FIG. 16 schematically shows a further element of the present disclosure.

Current fetal monitors cover a wide variety of measurable physiological parameters. Above all is the parameter set of fetal heart beat and uterine activity. This major pair of parameters may be supplemented by various maternal parameters like blood pressure, oxygen saturation, pulse and temperature.

Conventional, non-invasive methods for externally monitoring a fetus in a pregnant woman contain an Ultrasound Doppler transducer for measuring the Fetal Heart Rate (FHR), and a pressure transducer called tocodynamometer (Toco) for measuring uterine activity/contractions. Both transducers are held in place on the abdomen of the mother by an elastic belt fitted around the waist.

The Ultrasound Doppler transducer is based on the principle that, high frequency sound waves reflect mechanical action of the fetal heart. The mechanical contraction of the fetal heart muscle leads to periodic signal patterns in the ultrasound reflection. The period of the patterns is used by fetal monitors to determine the fetus' current heart rate. The ultrasound transducers use arrays of piezo elements as an electro mechanical converter. The array of piezo elements operates bi-directional as transmitter and receiver. A sequencer controls the timely switch over between transmit and receive phase. During the transmission phase the piezo array is repetitively excited in order to generate ultrasonic wave packets which are traveling towards the fetal heart. These traveling wave packets are reflected and frequency shifted due to the Doppler effect on moving layers in the body of the pregnant woman, for example at the fetal heart. While travelling down to the point of reflection and back to the transducer, the wave packets have to pass different organic structures like, muscle tissue, fat layers or amniotic fluid. These structures have different sizes and different damping ratios. Fat for example has a 3 to 4 times higher absorption factor than water. It is obvious that large layers of fat heavily influence the performance of an ultrasound transducer. In order to facilitate the ease of monitor handling and its connected transducers the manufacturers avoid control elements for adjustments. The transducers are designed to have an optimal performance on patients having a normal weight. With the increasing number of extremely overweighed and extremely underweighted patients, transducers following the principle "one fits all" simply exhibit a weak or bad performance if applied to women which do not fit to the "normal" range. Another aspect where transducer designed for use under normal conditions exhibit a disappointing performance is the use outside of the recommended limits. The recommended starting point for fetal heart rate examination with pulsed ultrasound Doppler is approximately the $25^{th}$ week of gestation. Some countries increasingly start CTG examination at the $20^{th}$ week of gestation and earlier. Depth placement and size of the fetal heart under this condition are significantly different compared to $30^{th}$ week of gestation. For a sufficient registration of the fetal heart in early weeks of gestation a narrow ultrasound beam with a depth range of sensitivity between 3 and 8 cm is normally advisable. If the early weeks of gestation are combined with overweight the depth range and the ultrasound beam energy must be increased. In order to allow individual adaptations to cover also extreme ranges of use, ultrasound beam energy, beam shape, range of sensitivity etc. could be made adjustable for the user. Experienced and well trained operators may be able to use the available adjustments in a meaningful way, but a standard operator may be confused. As mentioned before adding adjustable settings may be desirable by people doing research, but not for the standard user. A CTG is a device which must reliably work under all conditions with a minimum level of user interaction and a minimum level of knowledge about the mode of operation. For this reason simply adding additional control and adjustment elements is not the way to extend the range of operation. Based on surrounding information, which is available in many cases either in electronically stored records or as barcodes or other media the device can change its configuration automatically for this session to achieve an optimum performance. Nowadays CTG monitors provide start-up menus where the input of patient data is requested. The so called admit/discharge (ADT Admit, Discharge, Transfer) menu requests patient demographics. The content of the patient demographics is subject of definition. Normally patient name, week of gestation etc. are requested on patient admittance. This information is partly displayed on the monitor screen and printed on the paper strip. With monitors connected to an archiving and surveillance system the data required for admit is retrieved from a data base and automatically loaded to the monitor if the patient is assigned to a certain bed. The extent of the ADT data set is subject of free definition. In the context of the present invention it should preferably contain at least information on week of gestation, BMI or alternatively height and weight, country e.g. USA or Japan, Twins, triplets (this information could also be derived from the number of connected transducers).

By reading this information the monitor can categorize the data for example the BMI in two or more groups. Based on these categories the monitor is able to configure the various parameters of the data acquisition, signal amplification, filtering and signal processing chain individually to achieve best CTG registration results. For example, for a patient with high BMI (=category obese) and early weeks of gestation (<$25^{th}$ week=category premature) the monitor would adjust the ultrasound beam shape to narrow, the beam intensity to high, the expected depth range to medium/far. All this is done automatically in the background without user interaction. Again, the possible changes for an ultrasound transducer are exemplary. For all other parameters e.g. Toco, maternal pulse the same adaptive alterations in the data acquisition and signal processing path are possible. With the availability of ADT data, patient aware transducer control has the advantages of optimized signal acquisition and processing of all parameters, no or low operator interaction required, reduced exposure to energy fields (ultrasound), no increase in the complexity of use and being at least in parts retrospectively applicable to the installed base of transducers by software upgrade.

In the present context, a fetal monitor 74 with the connected transducers 75 is connected to a centralized surveillance and archiving system 72 with a data base 73. A patient is admitted to a certain monitor or bed with a local terminal or PC 71 also connected to the surveillance system 72. The application, running on the PC or Terminal provides a mask 70 for patient data as a part of the admittance procedure. When admitting a patient the mask must be filled out completely. The relevant data contains the information for the transducer 75 and signal processing control (inside 74 or 75) and is stored in the data base 20. The data set is populated to the monitor 74 where the patient is assigned to. The monitor 74 may use the data for instance if the signal processing or parts of the signal processing are done in the monitor 74. If the signal processing is done in active transducers 75, which may be wired or wireless, the monitor 74 makes sure that the relevant information is distributed to each connected transducer 75. The admittance/assignment procedure ensures that the data acquisition and signal processing procedures are automatically adapted to the settings defined by the ADT data.

Figure 17:
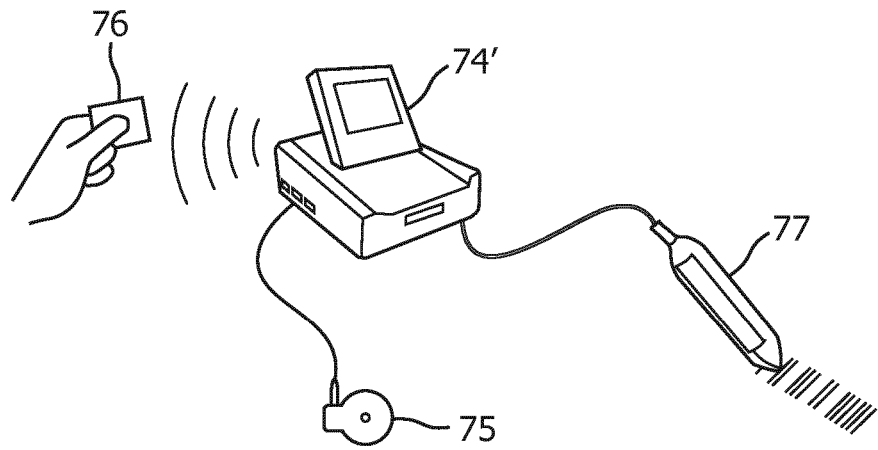

FIG. 17 schematically shows another element of the present disclosure.

In the context of this element, a near field communication path is provided for data exchange. The near field communication device can either be part of the monitor 74' or a separate device connected by wire to the monitor 74'. The relevant ADT data is, together with possible other information, stored in an individually programmed ID tag or card 76. The admission process is started by bringing the tag into the proximity of the NFC device 74'. In the following step the ADT data, stored on the card 76, is read and populated to the relevant parts of the monitoring system 74', 75.

In addition (or as an alternative), barcode tags containing ADT data can be read by an attached barcode reader 77.

Figure 18:
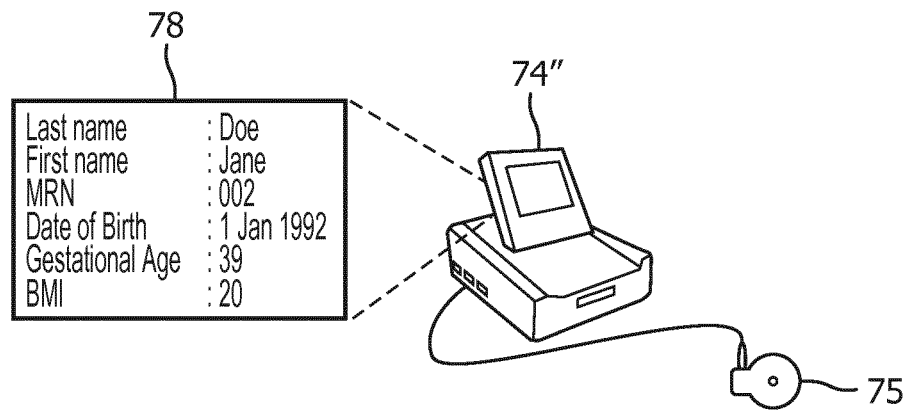

FIG. 18 schematically shows yet further element of the present disclosure.

This element uses the, in many monitors 74", already available possibility for direct entry of ADT data by filling out a form sheet 78 during patient admit. The data is entered manually by touch screen, keyboard or mouse is then as discussed above populated to the relevant parts of the monitor 74" or transducer 75.

Figure 19:
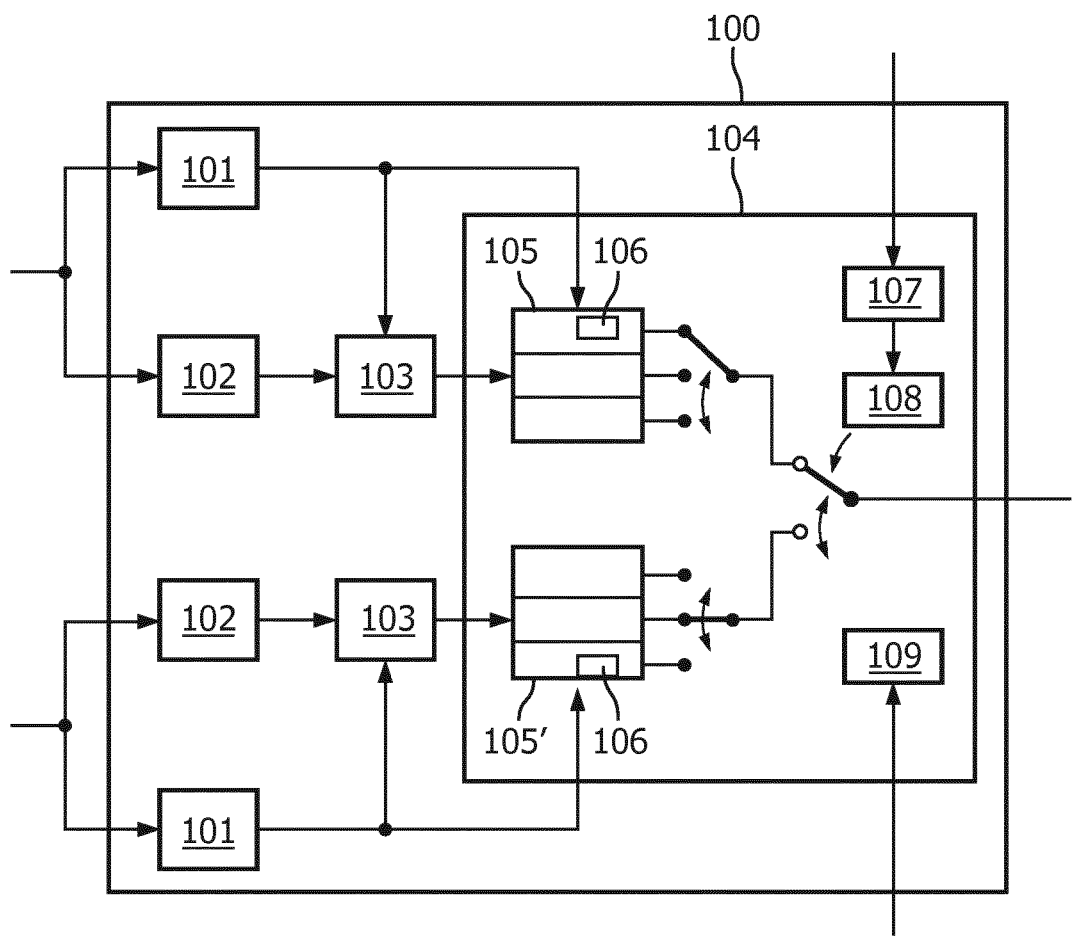

FIG. 19 schematically shows a processing device 100 in accordance with another embodiment of the invention.

The processing device 100 includes a reference demodulation unit 101, a phase shift demodulation unit 102, a comparison unit 103 and a processing unit 104.

The reference demodulation unit 101, the phase shift demodulation unit 102 and the comparison unit 103 are provided in duplicates, respectively, so to provide for two channels.

The reference demodulation units 101 are provided with an ultrasonic Doppler echo signal, from the respective channels, wherein each reference demodulation unit demodulates the received echo signal using the carrier frequency of the ultrasonic signal used for generating the echo signal as a demodulation frequency and outputs the respective reference demodulated signal to the comparison units 103 and to the processing unit 104. Similarly, the phase shift demodulation units 102, respectively, are receiving the respective ultrasonic Doppler echo signal and demodulate the echo signal using the demodulation frequency, however shifted by 90 degrees in comparison to the reference demodulation unit, and output the phase shift demodulated signal to the corresponding comparison unit 103.

Each comparison unit 103 is, as indicated above, provided with the reference demodulated signal and the phase shift demodulated signal for one of the channels and obtains information on a time-wise relation between corresponding respective signal points of the reference demodulated signal and the phase shift demodulated signal, wherein these respective signal points in the present embodiment are zero crossings (see FIG. 4) of the reference demodulated signal and the phase shift demodulated signal. As mentioned above, while the signal points considered in this context are zero crossings of the signals, nevertheless other points may be considered in the alternative or in addition, e.g. points of maximum positive and/or negative amplitude.

The information on a time-wise relation between the respective zero crossings for the first and second channel and the reference demodulated signals for the first and second channel are provided to the processing unit 104.

The processing unit 104 includes two processing sections 105, 105', an input section 107, a choosing section 108 and a setting unit 109. The respective processing sections 105, 105', one of which is provided for the first channel, while the other one is provided for the second channel are provided, respectively, for three different approaches on determining the fetal heart rate.

According to a first approach, the information on the time-wise relation between the respective signal points is directly used for obtaining the fetal heart rate, as already this information includes the periodicity indicative of the fetal heart rate.

According to a second approach, the information on the time-wise relation is used for cutting out portions of the reference demodulated signal, such that from such cut out demodulated signal the fetal heart rate is obtained by means of autocorrelation.

In the third approach, additionally autocorrelation is provided on the reference demodulated signal, basically according to a conventional approach, where the heart rate obtained by the second approach is compared with the result and a selection section 106 of the processing sections 105, 105' is arranged to determine the fetal heart rate by selecting either the conventionally determined heart rate or the cut heart rate.

The processing unit 104 is arranged such that for each channel the respective approach may be selected, thus providing an output for the respective channel. The input section receives external information on the fetal heart rate to be determined or on a heart rate other than the fetal heart rate to determined, namely the maternal heart rate and is connected to the choosing section 108. The choosing section is arranged to select either the heart rate determined according to the first channel or the heart rate determined to the second channel as the fetal heart rate to be determined based on the external information.

Furthermore, as indicated above, the processing unit 104 includes a setting unit 109, wherein this setting unit is arranged to receive patient related data and to adjust the setting of the processing unit based on the received patient related data.

In the present embodiment the processing device 100 is provided for processing two separate channels, even though it is also possible that more than two channels are processed. Furthermore, it is also not necessary that all three approaches discussed above are addressed in the processing unit, as only one or two of the discussed approaches or a different approach may be employed in the processing unit.

The output of the demodulation units 101 shown in FIG. 19 might be subjected to processing by an integrator and a high pass, band pass filter combination (not shown), while such elements may also be included in the demodulation units.

Figure 20:
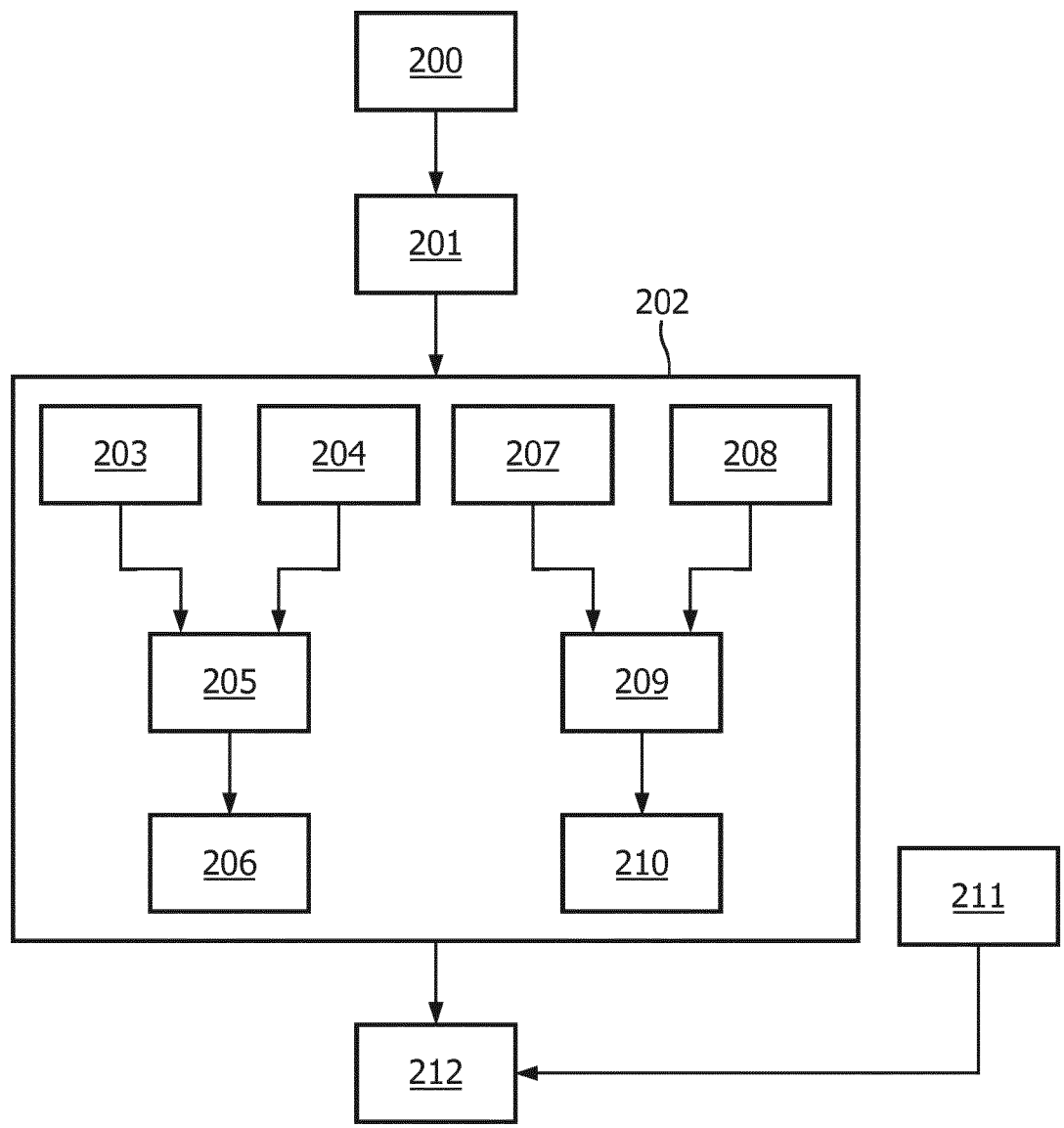
FIG. 20 shows a schematic flow diagram illustrating a method for determining a fetal heart rate in accordance with an embodiment of the invention, FIG. 21 schematically shows a processing device in accordance with yet another embodiment of the invention in a channel mode, and FIG. 22 schematically shows the processing device of FIG. 21 in a phase-shift mode.

FIG. 20 shows a schematic flow diagram illustrating a method for determining a fetal heart rate in accordance with an embodiment of the invention.

Similar to the embodiment discussed above with respect to FIG. 19, the discussion of FIG. 20 provides for a parallel obtaining of information by means of two channels, even though the present invention is not limited to this and may make use of more than two channels.

After a receiving step 200 of receiving patient related data, there is provided an adjustment step 201, in which the setting data relevant to the operation of the embodiment is adjusted based on the received patient related data. This is followed by a channel heart rate determining step 202. The channel heart rate determining step 202 includes determining a first heart rate from a first channel of the ultrasonic Doppler echo signal and a determining of a second heart rate from the second channel of the echo signal. The determining of the first heart rate includes a reference demodulation step 203, a phase shift demodulation step 204, a comparison step 205 and a processing step 206. Similarly, also the determining of the second heart rate includes a reference demodulation step 207, a phase shift demodulation step 208, a comparison step 209 and a processing step 210.

The steps 207 to 210 basically correspond to the steps 203 to 206 and therefore discussion is only provided for the latter.

In the reference demodulation step 203, the ultrasonic Doppler echo signal is demodulated using the carrier frequency of the ultrasonic signal used for generating the echo signal as the demodulation frequency, while correspondingly in the phase shift demodulation step 204 the echo signal is demodulated with a shift of 90 degrees.

In the comparison step 205 the resulting reference demodulated signal and phase shift demodulated signal are compared and information on a time-wise relation between the corresponding respective signal points, which, again, are the zero crossings of the reference demodulated signal and the phase shift demodulated signal is obtained. This information is used in the processing step 206 in a process of determining the fetal heart rate.

In an input step 211, external information on the fetal heart rate is received, which in this case is information on the maternal heart rate obtained separately and independently. In a choosing step 212 one of the heart rates determined by use of either channel is selected as the fetal heart rate to be determined and outputted correspondingly.

Figure 21:
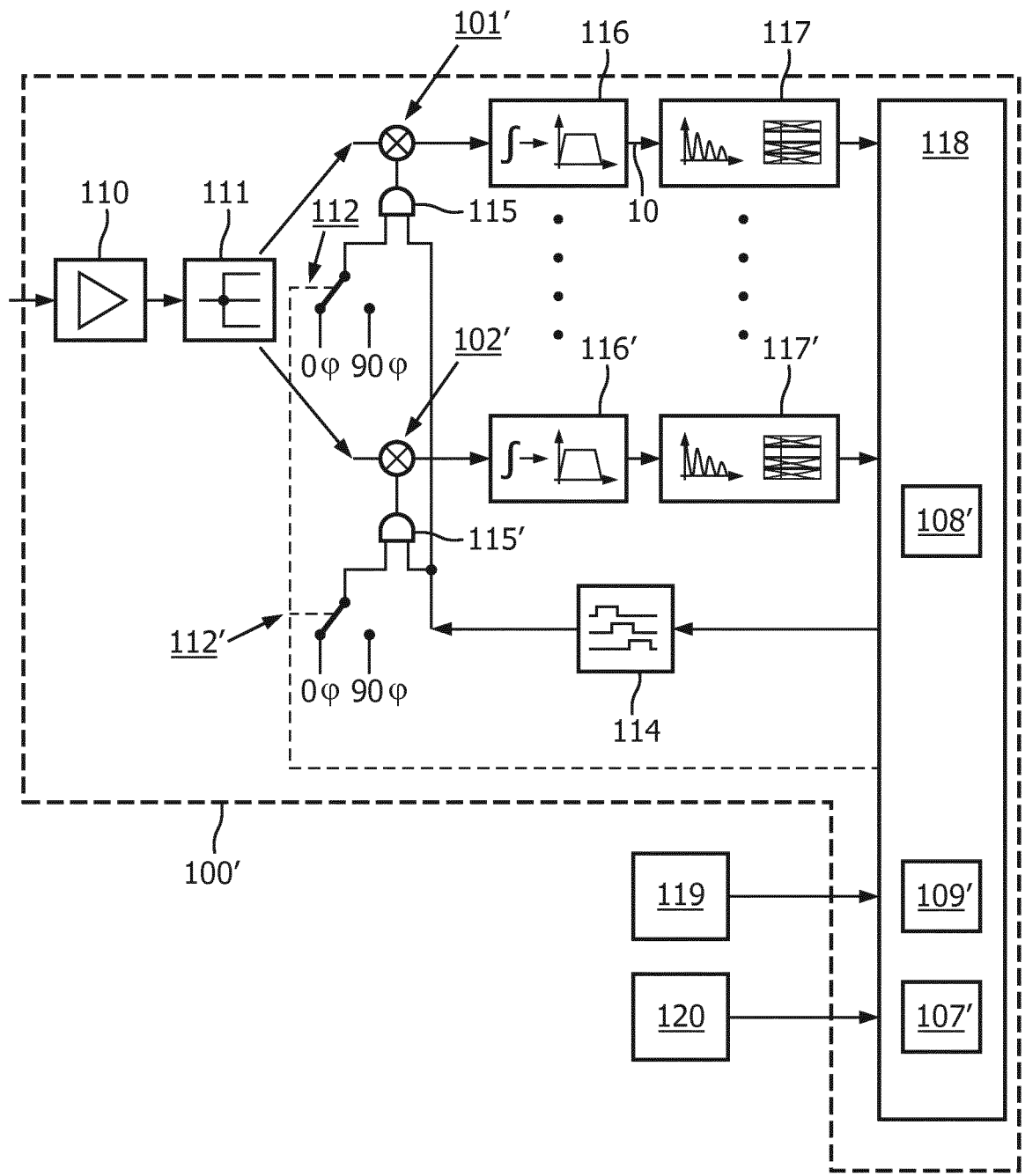

FIG. 21 schematically shows a processing device 100' in accordance with yet another embodiment of the invention in a channel mode.

The processing device 100' includes a high frequency amplifier 110 and a splitter 111. The splitter provides the signal into a number of sub-signals provided to the processing chains of the processing device 100'. In the illustration only two chains are shown even though any higher number may be provided as well. Each chain includes a synchronous demodulation unit 101', 102', which has a switchable demodulation clock 112, 112'.

The processing device 100' further includes a timing section 114, providing channel selection information in form of gating signals (timing signals for depth selection/measurement volume selection). The respective gating signals are provided for gating the demodulation signals by means of respective AND gates 115, 115'.

Each chain further includes an integration and band pass filter unit 116, 116' receiving the signal from the demodulation and providing a rectified and smoothed signal to a processor 117, 117' which is provided for autocorrelation and heart rate evaluation.

The output of the chains is provided to a control unit 118, which includes an input section 107', a choosing section 108' and a setting section 109'.

The input section 107' is coupled to an external source 120 of information on, for example, a maternal heart rate or depth ranges of other ultrasound transducers or a combination of both. It is to be noted that the external information may be also related to other heart rates to be excluded (e.g. an independently determined fetal heart rate of another twin). It is even conceivable that the independently obtained external information is not related to a heart rate to be disregarded but to the fetal heart rate of interest.

The setting section 109' is coupled to an external data base 119 providing patient related data.

Similar to the embodiments discussed above, the choosing section 108' is arranged to choose a channel (i.e. a processing chain) providing the fetal heart rate.

In the mode shown in FIG. 21, no phase shifting is provided for the demodulation and basically each processing chain addresses a different channel.

Figure 22:
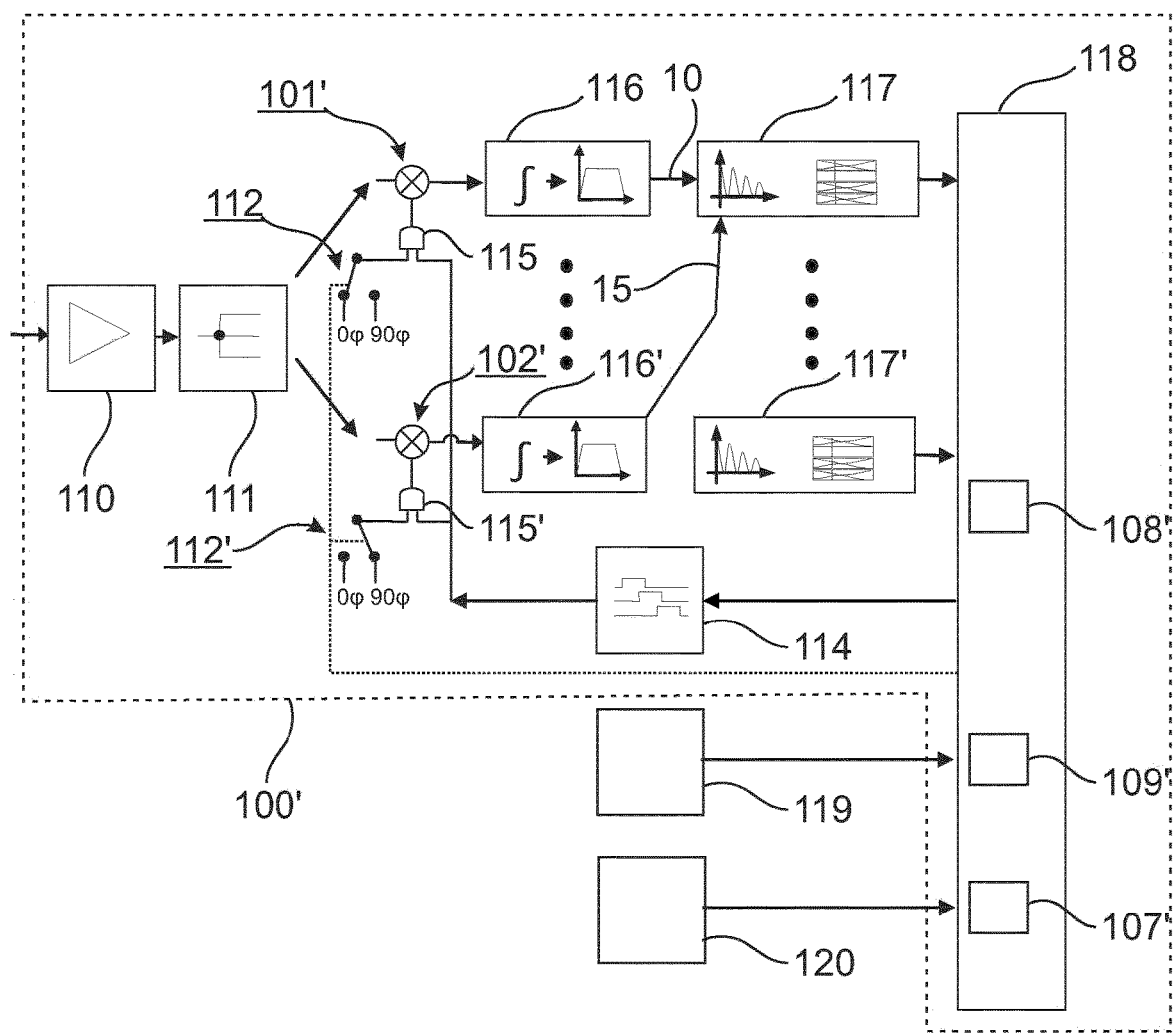

FIG. 22 schematically shows the processing device 101' of FIG. 21 in a phase-shift mode.

In contrast to the case of FIG. 21, for the demodulation unit 102' a demodulation frequency is provided by the demodulation clock 112', which is shifted in phase by 90 degree in comparison to the case of demodulation clock 112.

Furthermore, the resulting phase shift demodulated signal is provided to the processor 117, which compares the reference demodulated signal provided by the demodulation unit 101' and the phase shift demodulated signal so to obtain information on the time-wise relation between corresponding respective signal points of the reference demodulated signal and the phase shift demodulated signal, as it is already discussed above for other embodiments and elements of the present disclosure.

It is advantageous to split the volume of sensitivity covered by an ultrasound Doppler sensor into several sub volumes. It is furthermore desirable, as it becomes apparent from the present application, to avoid possible double counting by using a quadrature demodulation in parallel to a standard synchronous demodulation. Combining both methods in one signal processing unit with multiple channels allows reducing the number of required channels, because the channel functionality is individually adaptable to different situations. At least the first part of a channel, comprising the demodulator, integrator, filtering bench and the AD converter are until now build up in hardware. For this reason keeping the number of channels low is not only a cost advantage. Even if in the future everything is done digitally, keeping the complexity of an integrated circuit low has positive effects on power consumption, cost and chip size.

As indicated above, in the illustration of FIG. 21 and FIG. 22, to keep the example simple, only two channels are shown, even though it is to be noted that the number of channels is not limited. A suitable number of channels is, for example, four. As shown in FIG. 21 and FIG. 22 the received ultrasound signal is amplified by a high frequency amplifier 110. A splitter 111 splits the signal into two to N sub signals. Each sub signal is fed into an—in this case—identical signal processing chain. This chain starts with a synchronous demodulation unit 101', 102' which has a switchable demodulation clock 112, 112'. The controllable switch either selects a 0 degree phase shifted or a 90 degree phase shifted reference clock for demodulation. The demodulation signal is furthermore gated by use of an AND gate 115, 115' with a gating signal. The gating signal defines the depth sensitivity, respectively volume of sensitivity. The start point and the end point relatively to the end of the transmission period are freely definable for each channel. This allows having the volume segments either separated or overlapping. After demodulation the signal is integrated, band pass filtered (elements 116, 116'), rectified and smoothened in order to prepare the signal for autocorrelation in processor 117, 117'.

The control unit 118 at the end of the multiple signal processing chains is responsible for selecting the channel which most likely measures the fetal heart rate. A reliable method for selecting a heart rate from a plurality of heart rates is to compare the heart rates with a heart rate coming from a known source for instance derived by an ECG, as an example of an external source 120. Channels having similar heart rate values to the heart rate from the known source are excluded. The excluded channels are so to say free and do not contribute to the measurement accuracy.

This approach allows having flexible channels which can be reconfigured in order to increase the accuracy and reliability in a case that the control unit 118 realizes that a channel is in an idle state and not contributing meaningfully. In this case the control unit 118, for example, may set the depth range to the range of the channel which is actually measuring the fetal heart rate. It then may select the 90 degree phase shift signal for demodulation to allow a quadrature demodulation in order to obtain the direction of velocity. The sign of the velocity then could be used to cut out unwanted portions of the signal to avoid double counting. If more than two channels are available, another channel measuring none or a wrong heart rate could for instance be reprogrammed in a way that this channel additionally covers now the volume segment which was previously covered by the channel which is now doing the quadrature demodulation. The process of depth volume and functionality adaptation may be either statically or a dynamically controlled process done by the control unit.

Assigning the demodulation method and volume of sensitivity preferably takes into account patient related data. For instance in early weeks of gestation and a low BMI the algorithm would initially choose narrow volumes of sensitivity. Initially all channels are used for depth segmentation to find zones of activity. If the zones of activity have been identified the control unit 118 may change the functionality of a channel by changing for example the method of demodulation. The control unit may also influence amplification and filtering and as a factor, the rule set for extracting the heart rate out of the correlation result. Once the zones of activity are identified the control unit 118 might decide to put one or more channels aside the measuring channel. The parallel working channels must not necessarily have a different method of demodulation. Changing parameters, especially the rule set for determining the heart rate can result in a higher beat to beat accuracy especially in the upper heart beat frequency ranges.

Since the health personnel is accustomed to a certain appearance of the heart rate trace print out showing traces with a higher micro variability could cause confusion and rejection. Parallel working channels could provide data which are different from the usual way of presentation. This data could be used for calculations in the background to increase for example the confidence level that the ultrasound transducer picks up the fetal and not the maternal signal.

It should be noted that not necessarily all channels must have a switchable demodulation source. One channel might be sufficient, even though, in the case that the segment with QAM channel is the measurement and sound output channel a cracking noise may be audible when the measurement channel is moved to a different channel.

The present invention provides, among other facets, for an elimination of double counting heart rates by cutting out unwanted signal contributions, wherein particularly the heart rate selection may be improved further by comparing with a second heart rate calculated on basis of such signal with reduced information and/or by providing autocorrelation of a (binary) stream of signs indicating the phase information of the ultrasonic Doppler echo signal.

Another facet of the invention provides for an exclusion of a heart rate from multiple heart rates derived from a depth split ultrasound Doppler signal by comparison with a heart rate extracted from a second, independent source and/or mutual heart rate exclusion when measuring multiple heart rate signal with multiple ultrasound Doppler sensors.

A yet further facet of the invention provides for an adaptive signal processing and data acquisition controlled by patient related data, allowing for optimized energy emission e.g. in case of ultrasound transducers, optimized operating time in case of battery powered devices and transfer and distribution of patient related data to scattered signal processing and data acquisition units.

The present disclosure provides, in particular, for an ultrasound Doppler system having multiple depth segments, wherein each depth segment the heart rate is calculated individually and independently, while a decision unit is provided for excluding segments or heart rate values equal to a heart rate from a further individual or independent source. The individual or independent heart rate source may nevertheless be integrated into the same housing as (one of the) ultrasound transducers and might be for instance an IR sensor, accelerometer or the like. Also, the individual or independent source may be located in a spatially separated, second unit (e.g. an ECG or a blood pressure measurement unit). Preferably, the multiple ultrasound Doppler transducers exchange heart rate values and/or depth segments among each other via a cable or wireless connection.

Also provided is an ultrasound Doppler system having multiple depth segments with at least one depth segment which is supplied alternatively with a 90 degree phase shifted demodulation signal for IQ demodulation. The phase shifted demodulation channel could be permanently set aside for a heart rate calculation channel measuring the fetal heart rate. Further, any channel sorted out not to have a valid heart rate could be set aside a channel measuring the fetal heart rate.

According to the present disclosure, a system with multiple ultrasound Doppler transducers measuring multiple heart rates e.g. twins or triplets may be self-organizing in a way that heart activities measured by one transducer are not measured by the other transducers. This could be done by exchanging heart rate and depth segment values with broadcast messages or inter transducer data exchange.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single processor, device or other unit may fulfill the functions of several items recited in the claims. The mere fact that certain measures are recited in mutually different dependent claims does not indicate that a combination of these measures cannot be used to advantage.

Operations like demodulating, comparing, (information) processing, (signal) cutting or masking, performing autocorrelation, choosing, adjusting and providing of settings, receiving and transmitting can be implemented as program code means of a computer program and/or as dedicated hardware.

A computer program may be stored and/or distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A processing device to determine a fetal heart rate from an ultrasonic Doppler echo signal, comprising:
    a first processing section arranged to determine a first heart rate from a first channel of the ultrasonic Doppler echo signal, wherein the ultrasonic Doppler echo signal comprises at least two channels, the at least two channels including the first channel obtained for a first depth or a first depth range and a second channel obtained for a second depth or second depth range different from the first depth or the first depth range, and
    a second processing section arranged to determine a second heart rate from the second channel of the ultrasonic Doppler echo signal,
    an input section arranged to receive, from an additional heart rate determining device, maternal heart rate information other than the determined first heart rate and the determined second heart rate, and
    a choosing section arranged to select one of the determined first heart rate and the determined second heart rate as the fetal heart rate to be determined based on the maternal heart rate information from the additional heart rate determining device.

2. The processing device according to claim 1, wherein the processing device further comprises:
    a first demodulator arranged to demodulate the ultrasonic Doppler echo signal using a first channel selection information and a first input frequency based on a carrier frequency of an ultrasonic signal used to generate the ultrasonic Doppler echo signal as a demodulation frequency, thus providing a first demodulated signal, and
    a second demodulator arranged to demodulate the ultrasonic Doppler echo signal using a second channel selection information and a second input frequency based on the carrier frequency of the ultrasonic signal used to generate the ultrasonic Doppler echo signal as the demodulation frequency, thus providing a second demodulated signal;
    wherein the processing device is arranged to selectively operate in one of a channel mode and a phase-shift mode;
    wherein, in the channel mode, the first channel selection information indicates the first channel, the second channel selection information indicates the second channel and the first and second input frequency are identical; and
    wherein, in the phase-shift mode,
        the first channel selection information and the second channel selection information indicate a same channel, wherein there is a shift of 90 degrees in phase between the first and the second input frequency, and
        the first demodulator and the second demodulator are to function, respectively, as a reference demodulator and a phase shift demodulator, wherein the processing device compares the first and second demodulated signal to obtain information on a time-wise relation; and
    wherein the processing device is arranged to switch from the channel mode to the phase-shift mode in accordance with a selection of the choosing section, wherein the first and second channel selection information indicates which of the first and second channel are to provide the fetal heart rate.

3. A system to determine a fetal heart rate, comprising:
    an ultrasonic Doppler device arranged to transmit an ultrasonic signal and to detect an ultrasonic Doppler echo signal,
    a processing device coupled to the ultrasonic Doppler device to receive the detected ultrasonic Doppler echo signal, wherein the processing device includes:
        a first processing section arranged to determine a first heart rate from a first channel of the detected ultrasonic Doppler echo signal,
        a second processing section arranged being arranged to determine a second heart rate from a second channel of the detected ultrasonic Doppler echo signal, wherein the first channel is obtained for a first depth or a first depth range and the second channel is obtained for a second depth or a second depth range different from the first depth or the first depth range, an input section arranged to receive maternal heart rate information other than the determined first heart rate and the determined second heart rate, and a choosing section arranged to select one of the determined first heart rate and the determined second heart rate as the fetal heart rate to be determined based on the maternal heart rate information, an additional heart rate determining device arranged to determine an additional heart rate independently from the detected ultrasonic Doppler echo signal, the additional heart rate being a maternal heart rate other than the determined first heart rate and the determined second heart rate, and wherein the input section of the processing device is arranged to receive the maternal heart rate from the additional heart rate determining device.

4. The system according to claim 3, wherein the additional heart rate determining device includes one or more of:

an accelerometer arranged to measure maternal heart movements, an electrocardiograph arranged to measure maternal electrocardiography activity, a light sensor arranged to measure light absorption indicative of pulsating maternal oxygen saturation, a blood pressure sensor arranged to measure maternal blood pressure, and an additional ultrasonic Doppler device arranged to determine the additional heart rate.

5. A method to determine a fetal heart rate from an ultrasonic Doppler echo signal, comprising:

a channel heart rate determining operation of determining a first heart rate from a first channel of the ultrasonic Doppler echo signal and of determining a second heart rate from a second channel of the ultrasonic Doppler echo signal, wherein the ultrasonic Doppler echo signal comprises at least two channels, the at least two channels including the first channel obtained for a first depth or a first depth range and the second channel obtained for a second depth or a second depth range different from the first depth or the first depth range, an input operation of receiving, from an additional heart rate determining device, maternal heart rate information other than the determined first heart rate and the determined second heart rate, and a choosing operation of choosing one of the determined first heart rate and the determined second heart rate as the fetal heart rate to be determined based on the maternal heart rate information.

6. A non-transitory computer program product having computer readable code embodied therein, when executed by one or more processors, causes the one or more processors to:

determine a first heart rate from a first channel of an ultrasonic Doppler echo signal and determine a second heart rate from a second channel of the ultrasonic Doppler echo signal, wherein the first channel is obtained for a first depth or a first depth range and the second channel is obtained for a second depth or a second depth range different from the first depth or the first depth range, receive, from an additional heart rate determining device, maternal heart rate information other than the determined first heart rate and the determined second heart rate, and choose one of the determined first heart rate and the determined second heart rate as a fetal heart rate to be determined based on the maternal heart rate information from the additional heart rate determining device.

* * * * *